United States Patent
Bartmann et al.

[11] Patent Number: 5,403,512
[45] Date of Patent: Apr. 4, 1995

[54] VINYL COMPOUNDS, AND A LIQUID-CRYSTALLINE MEDIUM

[75] Inventors: Ekkehard Bartmann, Erzhausen; Herbert Plach, Darmstadt; Rudolf Eidenschink, Mainz; Volker Reiffenrath, Rossdorf; Detlef Pauluth, Darmstadt; Eike Poetsch, Mühltal; Sabine Schoen, Darmstadt; Volker Meyer, Gross-Zimmern; Michael Junge, Pfungstadt; Reinhard Hittich, Modautal, all of Germany

[73] Assignee: Merck Patent Gesellschaft Mit Beschrankter Haftung, Darmstadt, Germany

[21] Appl. No.: 916,006

[22] PCT Filed: May 26, 1992

[86] PCT No.: PCT/EP92/01185
§ 371 Date: Aug. 5, 1992
§ 102(e) Date: Aug. 5, 1992

[87] PCT Pub. No.: WO92/21734
PCT Pub. Date: Dec. 10, 1992

[51] Int. Cl.⁶ .............. C09K 19/52; C07D 239/02; C07C 43/02; G02F 1/13

[52] U.S. Cl. .............. 252/299.01; 252/299.61; 252/299.63; 252/299.64; 252/299.65; 252/299.66; 252/299.67; 544/303; 568/655; 568/661; 568/631; 359/103

[58] Field of Search .............. 252/299.01, 299.61, 252/299.62, 299.63, 299.64, 299.65, 299.66, 299.67; 359/103, 104; 568/631, 655, 661; 544/298, 303

[56] References Cited

U.S. PATENT DOCUMENTS

| | | | |
|---|---|---|---|
| 4,877,548 | 10/1989 | Kitano et al. | 252/299.63 |
| 4,880,562 | 11/1989 | Kitano et al. | 252/299.63 |
| 5,183,587 | 2/1993 | Kitano et al. | 252/299.63 |

*Primary Examiner*—Shean Wu
*Attorney, Agent, or Firm*—Millen, White, Zelano, & Branigan

[57] ABSTRACT

Vinyl compounds of the formula I

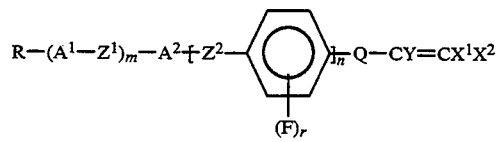

in which the variables are as described in the claims. The compounds are useful as components in liquid-crystalline media.

13 Claims, No Drawings

VINYL COMPOUNDS, AND A LIQUID-CRYSTALLINE MEDIUM

SUMMARY OF THE INVENTION

The invention relates to novel vinyl compounds of the formula I

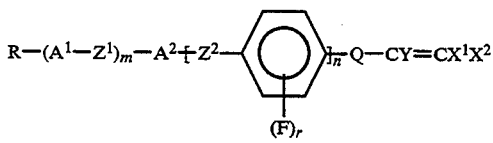

in which
R is H, an alkyl or alkenyl radical having 1 to 15 carbon atoms which is unsubstituted, monosubstituted by CN or $CF_3$ or at least monosubstituted by halogen, it also being possible for one or more $CH_2$ groups in these radicals to be replaced, in each case independently of one another, by —O—, —S—,

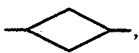

—CO—, —CO—O—, —O—CO— or —O—CO—O— in such a manner that oxygen atoms are not linked directly to one another, $A^1$ and $A^2$ are each, independently of one another, a
(a) trans-1,4-cyclohexylene radical in which, in addition, one or more non-adjacent $CH_2$ groups may be replaced by —O— and/or —S—,
(b) 1,4-phenylene radical in which, in addition, one or two CH groups may be replaced by N,
(c) radical from the group consisting of 1,4-cyclohexenylene, 1,4-bicyclo(2,2,2)octylene, piperidine-1,4-diyl, naphthalene-2,6-diyl, decahydronaphthalene-2,6-diyl and 1,2,3,4-tetrahydronaphthalene-2,6-diyl,
where the radicals (a) and (b) may be substituted by CN or fluorine, $Z^1$ and $Z^2$ are each, independently of one another, —CO—O—, —O—CO—, —$CH_2$O—, —O$CH_2$—, —$CH_2CH_2$—, —CH=CH—, —C≡C— or a single bond, and one of the radicals $Z^1$ and $Z^2$ is alternatively —$(CH_2)_4$— or —CH=CH—$CH_2CH_2$—, Q is a single bond, —O—, —$CH_2$—$CH_2$—, —C≡C—, trans-CH=CH—, —COO— or —$CH_2$O—, $X^1$ is H, F or Cl,
$X^2$ is F, Cl, $CF_3$, $OCF_3$, $OCHF_2$ or $SF_5$,
Y is H, F or Cl,
r is 0 to 4,
n is 0 or 1, and
m is 0, 1, 2 or 3, with the proviso
that, in the case where Y=H and Q=a single bond, $X^1$ and $X^2$ are Cl.

The invention furthermore relates to the use of these compounds as components of liquid-crystalline media, and to liquid-crystal and electro-optical display elements which contain the liquid-crystalline media according to the invention.

The compounds of the formula I can be used as components of liquid-crystalline media, in particular for displays based on the principle of the twisted cell, the guest-host effect, the effect of deformation of aligned phases or the effect of dynamic scattering.

The invention had the object of finding novel, stable liquid-crystalline or mesogenic compounds which are suitable as components of liquid-crystalline media and simultaneously have, in particular, a relatively low viscosity and relatively high dielectric anisotropy.

It has now been found that compounds of the formula I are eminently suitable as components of liquid-crystalline media. In particular, they have relatively low viscosities. They can be used to obtain stable liquid-crystalline media having a broad mesophase range and advantageous values for the optical and dielectric anisotropy. These media furthermore have good low-temperature behavior.

BACKGROUND OF THE INVENTION

Difluorostyrene derivatives and corresponding liquid-crystalline media, such as, for example, containing compounds of the formula

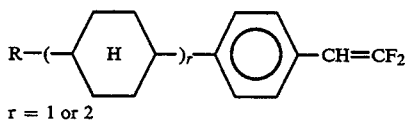

r = 1 or 2 have already been disclosed in EP 0 325 796 A1. However, these compounds tend to be chemically unstable due to illumination of HF.

Various compounds having liquid-crystalline properties and containing a terminal $CF_3$ group have already been disclosed (U.S. Pat. No. 4,330,426; U.S. Pat. No. 4,684,476; J. C. Liang and S. Kumar, Mol. Cryst. Liq. Cryst. 1987; Vol. 142, pp. 77–84). However, these compounds frequently have a highly smectogenic character and are less suitable for many practical applications.

However, in view of the very wide variety of areas of application of compounds of this type having a high Δε, it was desirable to have available further compounds which have properties precisely customized for the particular applications.

DETAILED DESCRIPTION OF THE INVENTION

In addition, the provision of compounds of the formula I very generally extends the range of liquid-crystalline substances which are suitable, from various application points of view, for the preparation of liquid-crystalline mixtures.

The compounds of the formula I have a broad range of applications. Depending on the choice of substituents, these compounds can be used as base materials from which liquid-crystalline media are predominantly composed; however, it is also possible to add compounds of the formula I to liquid-crystalline base materials from other classes of compounds in order, for example, to modify the dielectric and/or optical anisotropy of a dielectric of this type and/or to optimize its threshold voltage and/or its viscosity.

In particular, compounds of the formula I in which $X^1$=H and $X^2$=F are distinguished by their high clearing point at the same time as low viscosity. The vinyl ethers of the formula I (Q=O) have unusually high stability. In the pure state, the compounds of the formula I are colorless and form liquid-crystalline mesophases in a temperature range which is favorably located for electro-optical use. They are stable chemically, thermally and to light.

The invention thus relates to the compounds of the formula I and to the use of these compounds as components of liquid-crystalline media. The invention furthermore relates to liquid-crystalline media containing at least one compound of the formula I and to liquid-crystalline display elements, in particular electro-optical display elements, which contain media of this type.

Below, for reasons of simplicity, $A^3$ is a radical of the formula

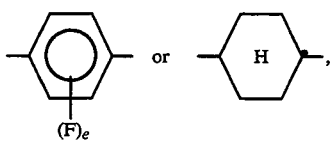

Cyc is a 1,4-cyclohexylene radical, Che is a 1,4-cyclohexenylene radical, Dio is a 1,3-dioxane-2,5-diyl radical, Dit is a 1,3-dithiane-2,5-diyl radical, Phe is a 1,4-phenylene radical, Pyd is a pyridine-2,5-diyl radical, Pyr is a pyrimidine-2,5-diyl radical and Bi is a bicyclo(2,2,2)octylene radical, it being possible for Cyc and/or Phe to be unsubstituted substituted or monosubstituted or disubstituted by F or CN. Z is $CY=CX^1X^2$.

$A^1$ and $A^2$ are preferably selected from the group consisting of Cyc, Che, Phe, Pyr, Pyd and Dio, it being preferred for only one of the radicals $A^1$ and $A^2$ present in the molecule to be Che, Phe, Pyr, Pyd or Dio.

Accordingly, the compounds of the formula I include bicyclic compounds of the subformulae Ia and Ib:

| | |
|---|---|
| R-$A^2$-$A^3$-Q-Z | Ia |
| R-$A^2$-$Z^2$-$A^3$-Q-Z | Ib |

Tricyclic compounds of the subformulae Ic to If:

| | |
|---|---|
| R-$A^1$-$A^2$-$A^3$-Q-Z | Ic |
| R-$A^1$-$Z^1$-$A^2$-$Z^2$-$A^3$-Q-Z | Id |
| R-$A^1$-$Z^1$-$A^2$-$A^3$-Q-Z | Ie |
| R-$A^1$-$A^2$-$Z^2$-$A^3$-Q-Z | If | and tetracyclic compounds of the subformulae Ig to Im:

| | |
|---|---|
| R-$A^1$-$A^1$-$A^2$-$A^3$-Q-Z | Ig |
| R-$A^1$-$Z^1$-$A^1$-$A^2$-$A^3$-Q-Z | Ih |
| R-$A^1$-$A^1$-$Z^1$-$A^2$-$A^3$-Q-Z | Ii |
| R-$A^1$-$A^1$-$A^2$-$Z^1$-$A^3$-Q-Z | Ij |
| R-$A^1$-$Z^1$-$A^1$-$Z^1$-$A^2$-$A^3$-Q-Z | Ik |
| R-$A^1$-$A^1$-$Z^1$-$A^2$-$Z^2$-$A^3$-Q-Z | Il |
| R-$A^1$-$Z^1$-$A^1$-$Z^1$-$A^2$-$Z^2$-$A^3$-Q-Z | Im |

Of these, those of the subformulae Ia, Ib, Ic, Id, Ie, If, Ii and Il are particularly preferred.

The preferred compounds of the subformula Ia include those of the subformulae Iaa to Iah:

| | |
|---|---|
| R-Phe-$A^3$-Q-Z | Iaa |
| R-Phe-$A^3$-Q-Z | Iab |
| R-Dio-$A^3$-Q-Z | Iac |
| R-Pyr-$A^3$-Q-Z | Iad |
| R-Pyd-$A^3$-Q-Z | Iae |
| R-Cyc-$A^3$-Q-Z | Iaf |
| R-Cyc-$A^3$-Q-Z | Iag |
| R-Che-$A^3$-Q-Z | Iah |

Of these, those of the formulae Iaa, Iab, Iac, Iad, Iaf and Iag are particularly preferred.

The preferred compounds of the subformula Ib include those of the subformulae Iba and Ibb:

| | |
|---|---|
| R—Cyc—CH$_2$CH$_2$—$A^3$—Q—Z | Iba |
| R—Cyc—COO—$A^3$—Q—Z | Ibb |

The preferred compounds of the subformula Ic include those of the subformulae Ica to Ico:

| | |
|---|---|
| R-Phe-Phe-$A^3$-Q-Z | Ica |
| R-Phe-Phe-$A^3$-Q-Z | Icb |
| R-Phe-Dio-$A^3$-Q-Z | Icc |
| R-Cyc-Cyc-$A^3$-Q-Z | Icd |
| R-Phe-Cyc-$A^3$-Q-Z | Ice |
| R-Cyc-Cyc-$A^3$-Q-Z | Icf |
| R-Pyd-Phe-$A^3$-Q-Z | Icg |
| R-Pyr-Phe-$A^3$-Q-Z | Ich |
| R-Phe-Pyr-$A^3$-Q-Z | Ici |
| R-Cyc-Pyr-$A^3$-Q-Z | Icj |
| R-Cyc-Phe-$A^3$-Q-Z | Ick |
| R-Cyc-Phe-$A^3$-Q-Z | Icl |
| R-Dio-Phe-$A^3$-Q-Z | Icm |
| R-Che-Phe-$A^3$-Q-Z | Icn |
| R-Phe-Che-$A^3$-Q-Z | Ico |

Of these, those of the formulae Ica, Icc, Icd, Ice, Ici and Icj are particularly preferred.

The preferred compounds of the subformula Id include those of the subformulae Ida to Idm:

| | |
|---|---|
| R-Phe-$Z^1$-Phe-$Z^1$-$A^3$-Q-Z | Ida |
| R-Phe-$Z^1$-Phe-$Z^1$-$A^3$-Q-Z | Idb |
| R-Phe-$Z^1$-Dio-$Z^1$-$A^3$-Q-Z | Idc |
| R-Cyc-$Z^1$-Cyc-$Z^1$-$A^3$-Q-Z | Idd |
| R-Cyc-$Z^1$-Cyc-$Z^1$-$A^3$-Q-Z | Ide |
| R-Pyd-$Z^1$-Phe-$Z^1$-$A^3$-Q-Z | Idf |
| R-Phe-$Z^1$-Pyd-$Z^1$-$A^3$-Q-Z | Idg |

| | |
|---|---|
| R-Pyr-Z¹-Phe-Z¹-A³-Q-Z | Idh |
| R-Phe-Z¹-Pyr-Z¹-A³-Q-Z | Idi |
| R-Phe-Z¹-Cyc-Z¹-A³-Q-Z | Idj |
| R-Cyc-Z¹-Phe-Z¹-A³-Q-Z | Idk |
| R-Cyc-Z¹-Phe-Z¹-A³-Q-Z | Idl |
| R-Dio-Z¹-Phe-Z¹-A³-Q-Z | Idm |

The preferred compounds of the subformula Ie include those of the subformulae Iea to Iel:

| | |
|---|---|
| R-Pyr-Z¹-Phe-A³-Q-Z | Iea |
| R-Dio-Z¹-Phe-A³-Q-Z | Ieb |
| R-Phe-Z¹-Phe-A³-Q-Z | Iec |
| R-Cyc-Z¹-Phe-A³-Q-Z | Ied |
| R-Cyc-Z¹-Phe-A³-Q-Z | Iee |
| R-Phe-Z¹-Cyc-A³-Q-Z | Ief |
| R-Cyc-Z¹-Cyc-A³-Q-Z | Ieg |
| R-Cyc-Z¹-Cyc-A³-Q-Z | Ieh |
| R-Phe-Z¹-Dio-A³-Q-Z | Iei |
| R-Pyd-Z¹-Phe-A³-Q-Z | Iej |
| R-Phe-Z¹-Pyr-A³-Q-Z | Iek |
| R-Cyc-Z¹-Pyr-A³-Q-Z | Iel |

The preferred compounds of the subformula If include those of the subformulae Ifa to Ifr:

| | |
|---|---|
| R-Pyr-Phe-Z¹-A³-Q-Z | Ifa |
| R-Pyr-Phe-OCH₂-A³-Q-Z | Ifb |
| R-Phe-Phe-Z¹-A³-Q-Z | Ifc |
| R-Phe-Phe-OOC-A³-Q-Z | Ifd |
| R-Phe-Phe-Z¹-A³-Q-Z | Ife |
| R-Cyc-Cyc-Z¹-A³-Q-Z | Iff |
| R-Cyc-Cyc-Z¹-A³-Q-Z | Ifg |
| R-Cyc-Cyc-CH₂CH₂-A³-Q-Z | Ifh |
| R-Pyd-Phe-Z¹-A³-Q-Z | Ifi |
| R-Dio-Phe-Z¹-A³-Q-Z | Ifj |
| R-Phe-Cyc-Z¹-A³-Q-Z | Ifk |
| R-Phe-Cyc-Z¹-A³-Q-Z | Ifl |
| R-Phe-Pyd-Z¹-A³-Q-Z | Ifm |
| R-Che-Phe-Z¹-A³-Q-Z | Ifn |
| R-Phe-Che-Z¹-A³-Q-Z | Ifo |
| R-Cyc-Phe-Z¹-A³-Q-Z | Ifp |
| R-Cyc-Phe-OOC-A³-Q-Z | Ifq |
| R-Cyc-Phe-Z¹-A³-Q-Z | Ifr |

R is preferably alkyl, furthermore alkoxy. $A^1$ and/or $A^2$ are preferably Phe, Cyc, Che, Pyr or Dio. The compounds of the formula I preferably contain not more than one of the radicals Bi, Pyd, Pyr, Dio or Dit.

Preference is also given to compounds of the formula I and of all subformulae in which $A^1$ and/or $A^2$ is 1,4-phenylene which is monosubstituted or disubstituted by F or monosubstituted by CN. These are, in particular, 2-fluoro-1,4-phenylene, 3-fluoro-1,4-phenylene, 3,5-difluoro-1,4-phenylene, 2-cyano-1,4-phenylene and 3-cyano-1,4-phenylene. In a particularly preferred embodiment, $A^2$ is 3,5-difluoro-1,4-phenylene, and m is 1 or 2.

$Z^1$ and $Z^2$ are preferably a single bond, —CO—O—, —O—CO— and —CH₂CH₂—, and secondarily preferably —CH₂O— and —OCH₂—.

$A^3$ is preferably or

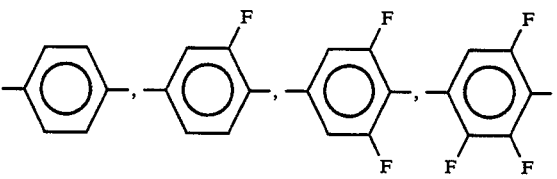

or

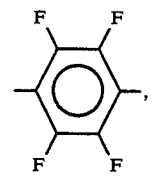

Z is preferably

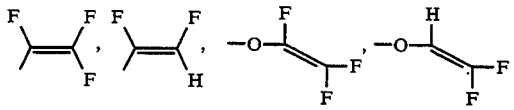

If one of the radicals $Z^1$ and $Z^2$ is —(CH₂)₄— or —CH=CH—CH₂CH²—, the other radical $Z^1$ or $Z^2$ (if present) is preferably a single bond.

Preferred compounds of this type conform to the subformula I'

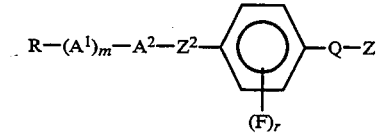

I' in which $Z^2$ is —(CH₂)₄— or —CH=CH—CH₂CH²—, and R, $A^1$, $A^2$, m, Q and Z are as defined above. The preferred meanings for R, $A^1$, $A^2$, m, Q and Z also correspond to those for the compounds of the formula I.

m is preferably 1 or 0, particularly preferably 0.

Particularly preferred compounds conform to the subformulae I1 to I10.

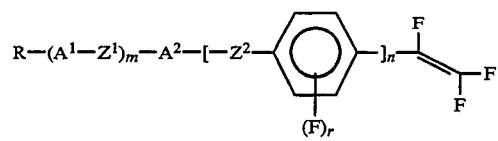 I1

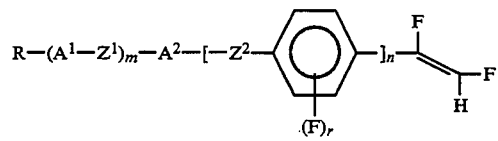 I2

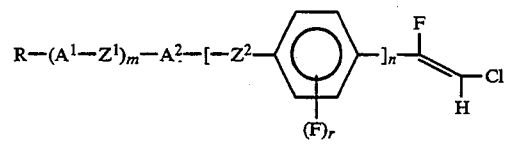 I3

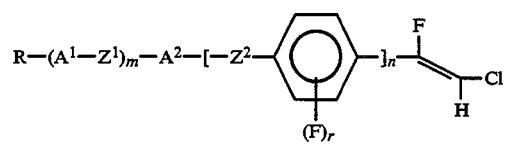 I3

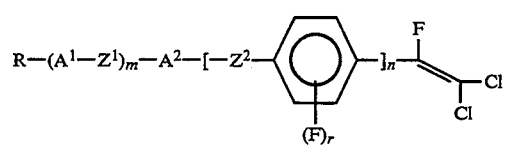 I4

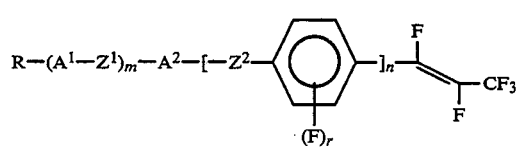 I5

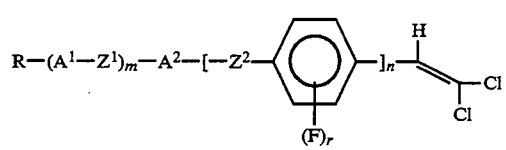 I6

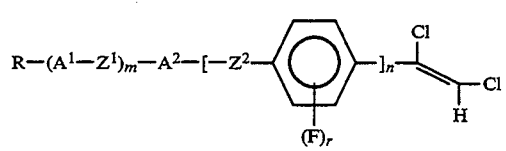 I7

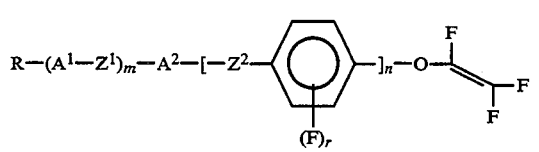 I8

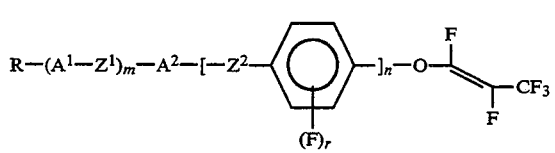 I9

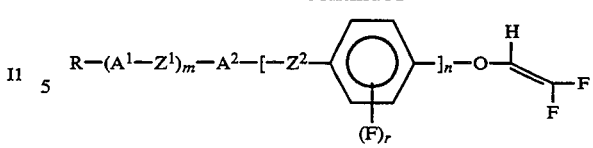 I10

If R is an alkyl radical and/or an alkoxy radical, this may be straight-chain or branched. It is preferably straight-chain, has 2, 3, 4, 5, 6 or 7 carbon atoms and accordingly is preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl is preferably straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8-or 9-oxadecyl.

If R is an alkyl radical in which one $CH_2$ group has been replaced by —CH=CH—, this may be straight-chain or branched. It is preferably straight-chain and has 2 to 10 carbon atoms. Accordingly, it is in particular vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5-or hept-6-enyl, oct-1-, 2-, 3-, 4-, 5-, 6-or oct-7-enyl, non-1-, 2-, 3-, 4-, 5-, 6-, 7- or non-8-enyl, or dec-1-, 2-, 3-, 4-, 5-, 6-, 7-, 8- or dec-9-enyl.

If R is an alkyl radical in which one $CH_2$ group has been replaced by —O— and one by —CO—, these are preferably adjacent. These thus contain an acyloxy group —CO—O— or an oxycarbonyl group —O—CO—. These are preferably straight-chain and have 2 to 6 carbon atoms. Accordingly, they are in particular acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)butyl.

If R is an alkyl radical in which one $CH_2$ group has been replaced by unsubstituted or substituted —CH=CH— and an adjacent $CH_2$ group has been replaced by CO or CO—O or O—CO—, this may be straight-chain or branched. It is preferably straight-chain and has 4 to 13 carbon atoms. Accordingly, it is in particular acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl or 9-methacryloyloxynonyl.

If R is an alkyl or alkenyl radical which is monosubstituted by CN or $CF_3$, this radical is preferably straight-chain and the substitution by CN or CF₃ is in the ω-position.

If R is an alkyl or alkenyl radical which is at least monosubstituted by halogen, this radical is preferably straight-chain, and halogen is preferably F or Cl. In the case of multiple substitution, halogen is preferably F. The resulting radicals also include perfluorinated radicals. In the case of monosubstitution, the fluorine or chlorine substituent may be in any desired position, but is preferably in the ω-position.

Compounds of the formula I which contain wing groups R which are suitable for polymerization reactions are suitable for the preparation of liquid-crystalline polymers.

Compounds of the formula I containing branched wing groups R may occasionally be of importance due to better solubility in the conventional liquid-crystalline base materials, but in particular as chiral dopes if they are optically active. Smectic compounds of this type are suitable as components of ferroelectric materials.

Compounds of the formula I having S$_A$ phases are suitable, for example, for thermally addressed displays.

Branched groups of this type generally contain not more than one chain branch. Preferred branched radicals R are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy and 1-methylheptoxy.

If R is an alkyl radical in which two or more CH₂ groups have been replaced by —O— and/or —CO—O—, this may be straight-chain or branched. It is preferably branched and has 3 to 12 carbon atoms. Accordingly, it is in particular biscarboxymethyl, 2,2-biscarboxyethyl, 3,3-biscarboxypropyl, 4,4-biscarboxybutyl, 5,5-biscarboxypentyl, 6,6-biscarboxyhexyl, 7,7-biscarboxyheptyl, 8,8-biscarboxyoctyl, 9,9-biscarboxynonyl, 10,10-biscarboxydecyl, bis(methoxycarbonyl)methyl, 2,2-bis(methoxycarbonyl)ethyl, 3,3-bis(methoxycarbonyl)propyl, 4,4-bis(methoxycarbonyl)butyl, 5,5-bis(methoxycarbonyl)pentyl, 6,6-bis(methoxycarbonyl)hexyl, 7,7-bis(methoxycarbonyl)heptyl, 8,8-bis(methoxycarbonyl)octyl, bis(ethoxycarbonyl)methyl, 2,2-bis(ethoxycarbonyl)ethyl, 3,3-bis(ethoxycarbonyl)propyl, 4,4-bis(ethoxycarbonyl)butyl and 5,5-bis(ethoxycarbonyl)hexyl.

Compounds of the formula I which contain wing groups R which are suitable for polycondensations are suitable for the preparation of liquid-crystalline polycondensates.

Formula I covers the racemates of these compounds and the optical antipodes, and mixtures thereof.

Of these compounds of the formula I and of the subformulae Ia-m, those are preferred in which at least one of the radicals present therein has one of the preferred meanings indicated.

In the compounds of the formula I, those stereoisomers are preferred in which the rings Cyc and piperidine are trans-1,4-disubstituted. Those of the abovementioned formulae which contain one or more groups Pyd, Pyr and/or Dio in each case cover the two 2,5-positional isomers.

Some very particularly preferred smaller groups of compounds are those of the subformulae II1 to II23 (L¹, L² and L³: H or F)

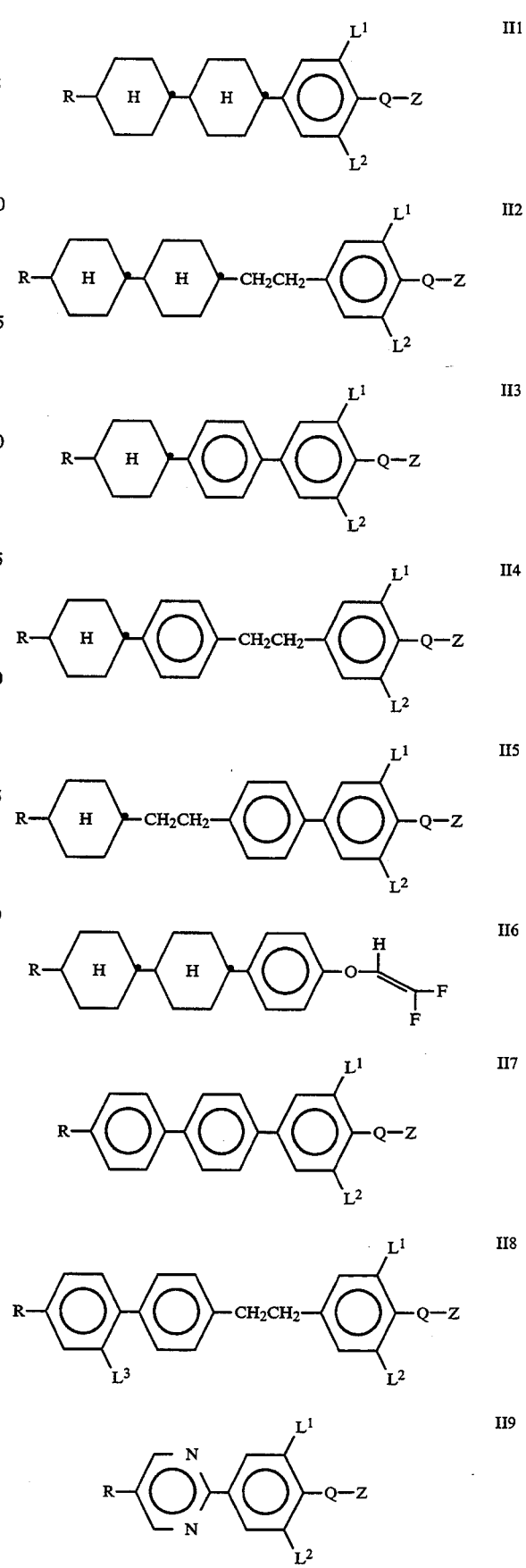

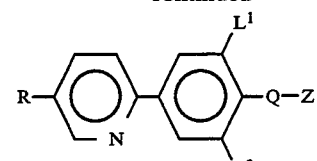
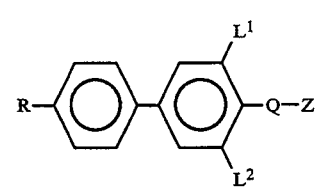
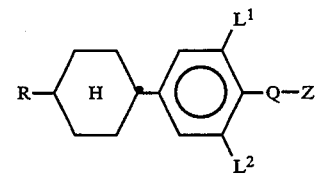
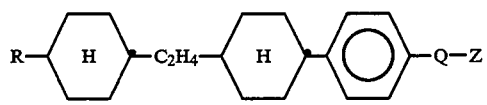
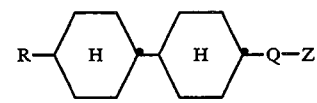
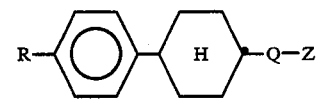
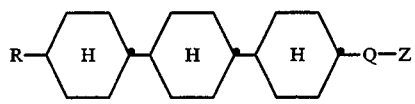
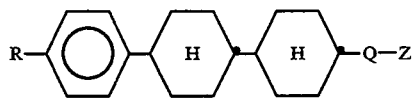
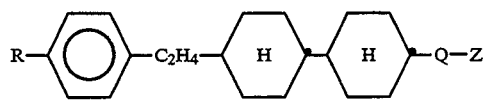
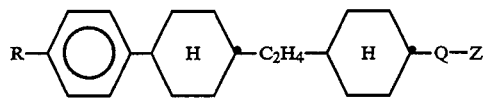
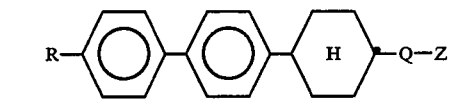
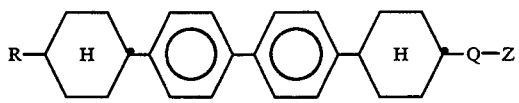

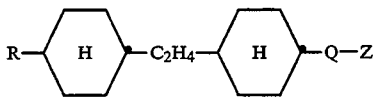

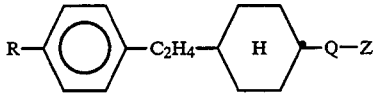

The 1,4-cyclohexenylene group preferably has the following structures:

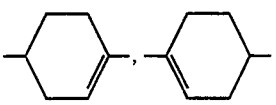

Likewise preferred are the compounds conforming to the subformulae I1 to I11, containing

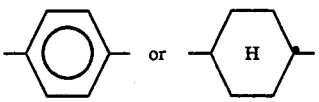

instead of

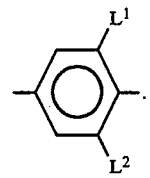

The compounds of the formula I are prepared by methods known per se, as described in the literature (for example in the standard works such as Houben-Weyl, Methoden der Organischen Chemie, Georg-Thieme-Verlag, Stuttgart, Vol. IX, pp. 867 ff.), to be precise under reaction conditions which are known and suitable for said reactions.

Use may also be made here of variants which are known per se, but are not described here in greater detail.

Vinyl compounds according to the invention can be prepared, for example, by metalating a compound of the formula II

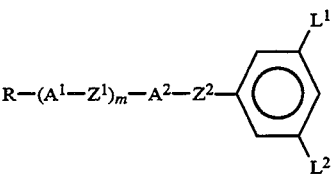

in which $L^1$ and $L^2$ are H or F, and R, $A^1$, $A^2$, $Z^1$, $Z^2$ and m are as defined above, in accordance with the reaction scheme below, and subsequently reacting with a suitable electrophile:

Scheme 1

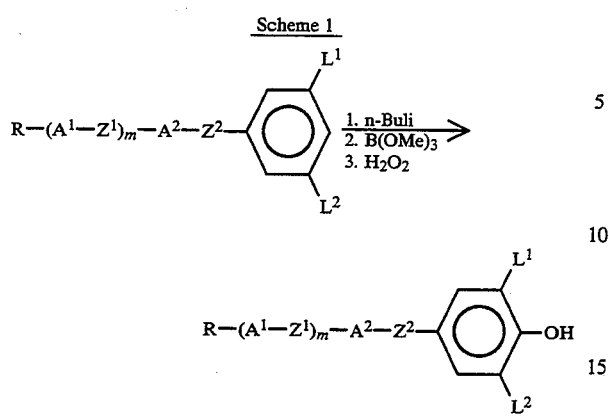

The target products where Q=O can be obtained from the resultant phenol by known methods, for example by reaction with tetrafluoroethylene and an equivalent amount of base (K. Okuhara et al., Bull. Chem. Soc. Japan. 35, 534 (1962); W. J. Pummer and L. A. Wall, SPE Transactions 3, 220 (1963) and Knunyants/Yakobson, Syntheses of Fluoroorganic Compounds, Springer 1985).

However, problems sometimes occur during purification due to the tetrafluoroethyl ethers formed as by-products, so that the base-induced elimination of HF from tetrafluoroethyl ether is suitable for the preparation of the trifluorovinyl ethers:

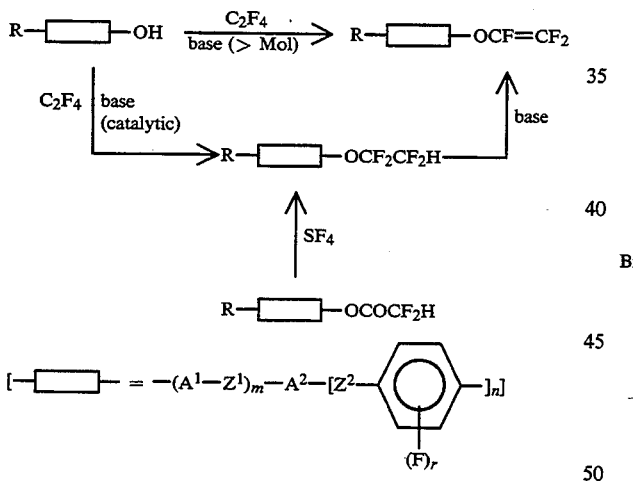

The indirect route via the tetrafluoroethyl ethers is more advantageous than the direct synthetic route, since the latter is afflicted with complications and gives product mixtures.

Other synthetic methods are evident to a person skilled in the art. For example, the radical R-$(A^1$-$Z^1)_m$-$A^2$-$Z^2$ can be introduced by reactions which are customary in liquid-crystal chemistry (for example esterification, etherification or couplings, for example as described in the article E. Poetsch, Kontakte (Darmstadt) 1988 (2), p. 15).

The compounds of the formula II can be prepared, for example, in accordance with the synthetic schemes below:

Scheme 2
(A = —($-A^1$—$Z^1$—$)_m$—$A^2$—/$Z^2$ = —CH$_2$CH$_2$—;

-continued
Scheme 2
$L^1$ = $L^2$: H or F)

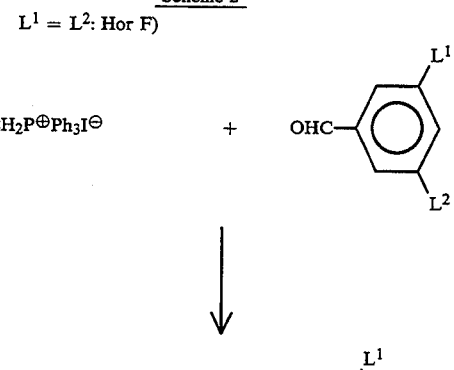

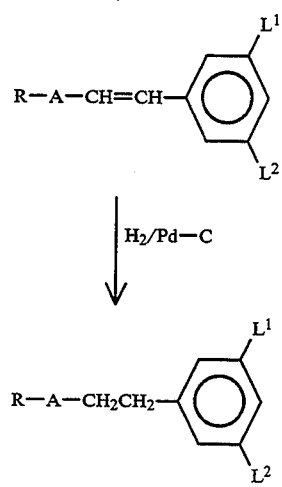

Scheme 3
(A = —($-A^1$—$Z^1$—$)_m$—$A^2$—/$Z^2$ = Single bond
$L^1$ — $L^2$: H or F)

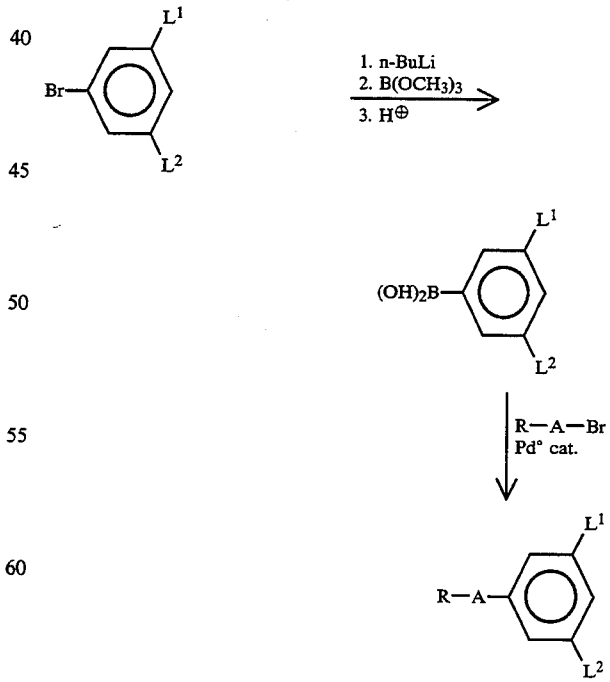

Scheme 4
(L = H or F)

-continued

Scheme 4

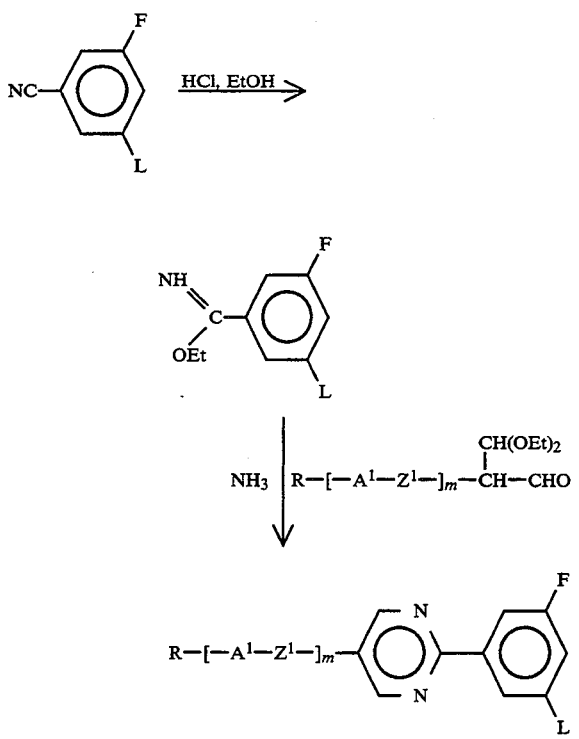

Scheme 5

(L = H or F)

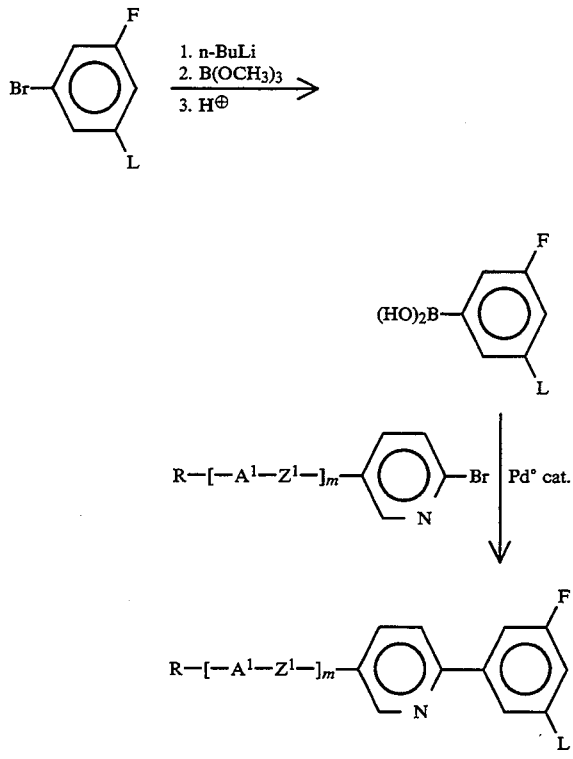

Scheme 6

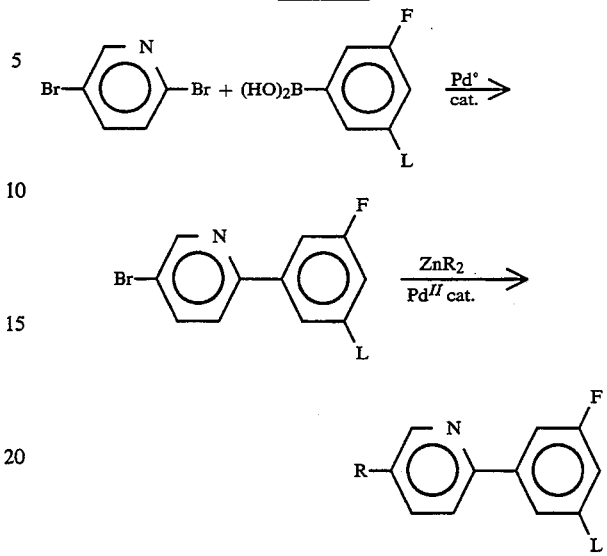

The starting materials are either known or can be prepared analogously to known compounds.

Esters of the formula I can also be obtained by esterification of corresponding carboxylic acids (or reactive derivatives thereof) using alcohols or phenols (or reactive derivatives thereof) or by the DCC method (DCC=dicyclohexylcarbodiimide).

The corresponding carboxylic acids and alcohols or phenols are known or can be prepared analogously to known processes.

In a further process for the preparation of the compounds of the formula I, an aryl halide is reacted with an olefin in the presence of a tertiary amine and in the presence of a palladium catalyst (cf. R. F. Heck, Acc. Chem. Res. 12 (1979) 146). Examples of suitable aryl halides are chlorides, bromides and iodides, in particular bromides and iodides. The tertiary amines, such as, for example, triethylamine, which are necessary for the success of the coupling reaction are also suitable as solvents. Examples of palladium catalysts are salts thereof, in particular (Pd(II) acetate, with organic phosphorus(III) compounds, such as, for example, triarylphosphines. The reaction can be carried out in the presence or absence of an inert solvent at temperatures between about 0° and 150°, preferably between 20° and 100°; examples of suitable solvents are nitriles, such as acetonitrile, or hydrocarbons, such as benzene or toluene. The aryl halides and olefins employed as starting materials are frequently commercially available or can be prepared by processes known from the literature, for example by halogenation of corresponding parent compounds or by elimination reactions of corresponding alcohols or halides.

In this way, stilbene derivatives, for example, can be prepared. Stilbenes may furthermore be prepared by reacting a 4-substituted benzaldehyde with an appropriate phoshorus ylide by the Wittig method. However, tolans of the formula I can also be prepared by replacing the olefin by monosubstituted acetylene (Synthesis 627 (1980) or Tetrahedron Lett. 27, 1171 (1986)).

Furthermore, aromatic compounds can be coupled by reacting aryl halides with aryltin compounds. These reactions are preferably carried out with addition of a catalyst, such as, for example, a palladium(0) complex, in inert solvents, such as hydrocarbons, at high temperatures, for example in boiling xylene, under a protective gas.

Coupling reactions of alkynyl compounds with aryl halides can be carried out analogously to the method described by A. O. King, E. Negishi, F. J. Villani and A. Silveira in J. Org. Chem. 43, 358 (1978).

Tolans of the formula I can also be prepared by the Fritsch-Buttenberg-Wiechell rearrangement (Ann. 279, 319, 1984), in which 1,1-diaryl-2-haloethylenes are rearranged to give diarylacetylenes in the presence of strong bases.

Tolans of the formula I can also be prepared by brominating the corresponding stilbenes and subsequently dehydrohalogenating the products. Use may also be made of variants of this reaction which are known per se, but are not described here in greater detail.

Ethers of the formula I are obtainable by etherification of corresponding hydroxyl compounds, preferably corresponding phenols, the hydroxyl compound expediently first being converted into a corresponding metal derivative, for example into the corresponding alkali metal alkoxide or alkali metal phenoxide by treatment with NaH, NaNH$_2$, NaOH, KOH, Na$_2$CO$_3$ or K$_2$CO$_3$. This can then be reacted with corresponding alkyl halide, alkyl sulfonate or dialkyl sulfate, expediently in an inert solvent, such as, for example, acetone, 1,2-dimethoxyethane, DMF or dimethyl sulfoxide, or alternatively with an excess of aqueous or aqueous-alcoholic NaOH or KOH, at temperatures between about 20° and 100°.

The starting materials are either known or can be prepared analogously to known compounds.

The compounds of the formula I' where $Z^2 = -(CH_2)_4-$ can be prepared in accordance with the scheme below:

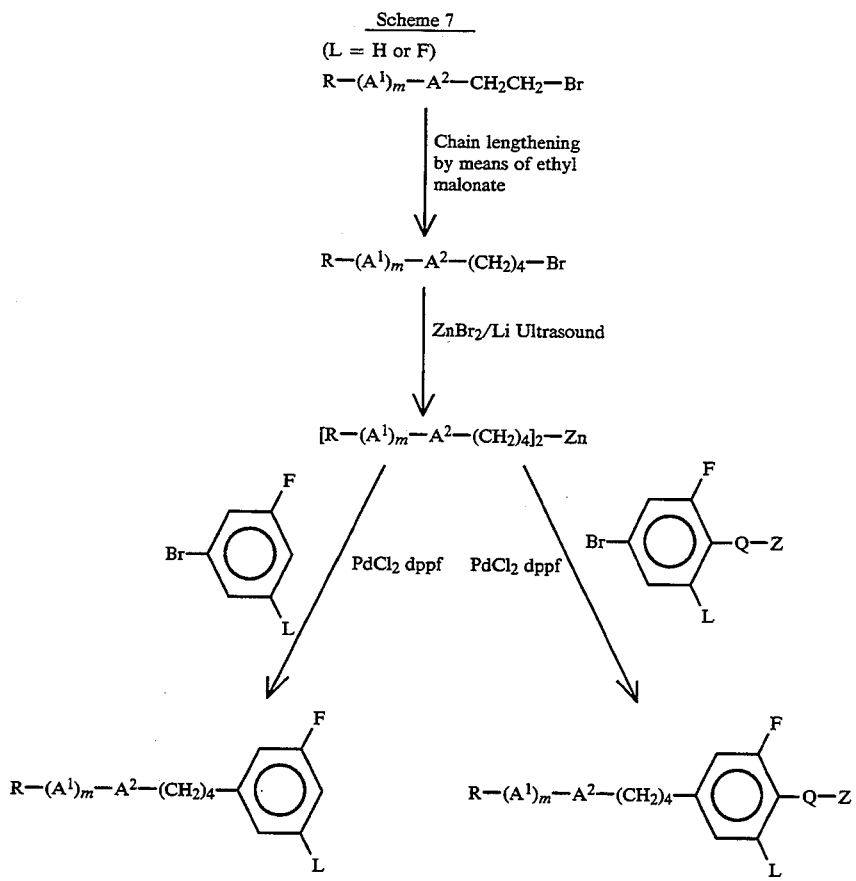

In the Pd(II)-catalyzed coupling reaction, either the target product I' is formed directly or a precursor into which the radical -Q-Z is introduced entirely analogously to the above methods for compounds of formula I is first formed.

The compounds of the formula I' where $Z^2 = -CH=CH-CH_2CH_2-$ can be prepared by the Wittig method in accordance with the scheme below:

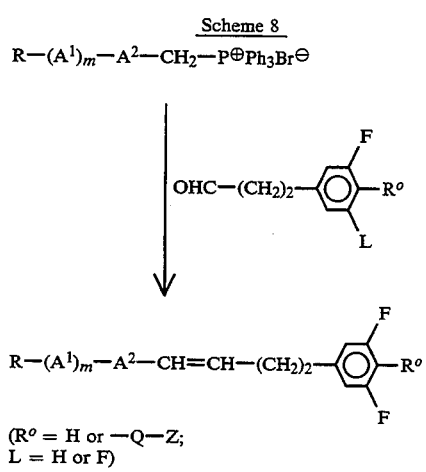

The preferred trans-isomers thereafter can be prepared by the isomerization methods known from the literature. The precursors where R°=H which may be obtained are converted into the compounds of the formula I' entirely analogously to the precursors of the compounds of the formula I by introduction of the radical -Q-Z.

The aldehydes can be obtained by the Heck reaction of appropriately substituted 1-bromo-3-fluorobenzene derivatives with allyl alcohol.

The trifluorovinyl compounds according to the invention (Y=F, X¹=X²=F) where Q=a single bond can be prepared by known synthetic methods:

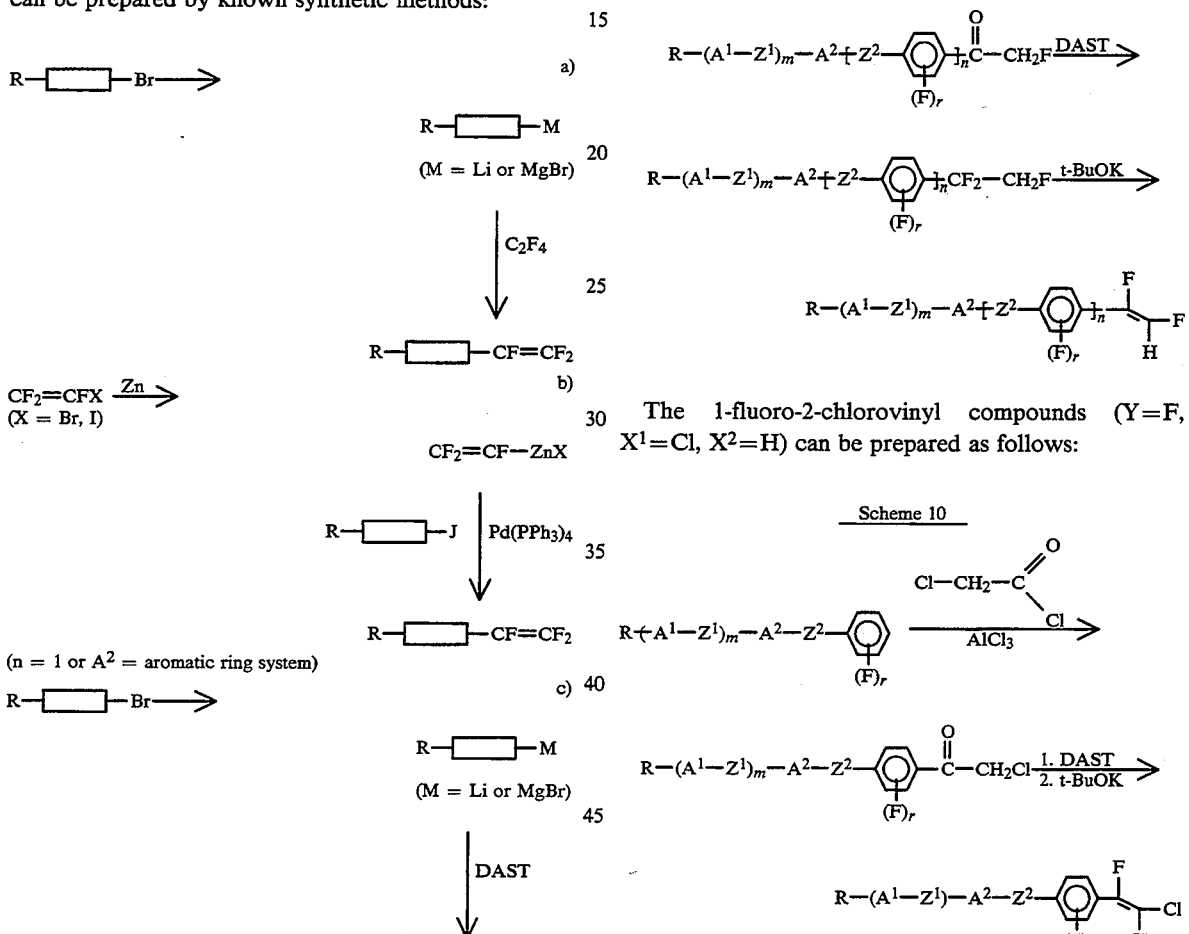

Further details concerning reaction conditions and starting materials are given in Houben-Weyl, Volume V/3, pp. 424–431; S. Dixon, J. Org. Chem. 21 (1956) 400; P. L. Hinze and D. J. Button, ebenda 53 (1988) 2714; DE-A 40 02 374 and DE-A 40 06 921.

The 1,2-difluorovinyl compounds (Y=F, X¹=H, X²=F) can be prepared in accordance with the reaction scheme below:

Scheme 9

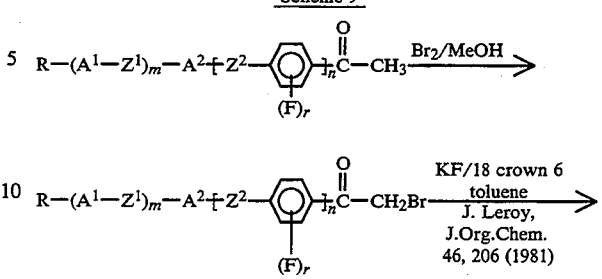

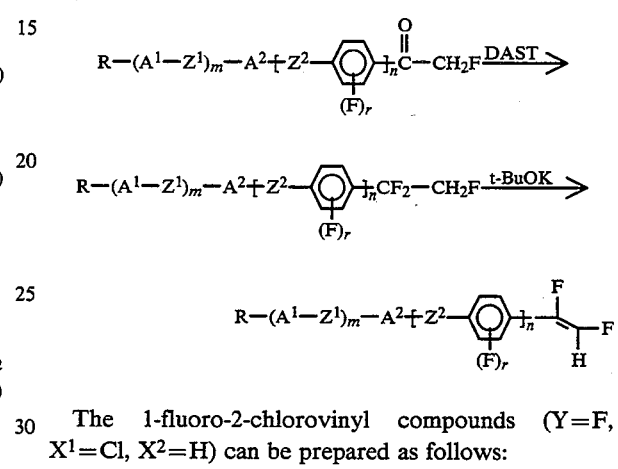

The 1-fluoro-2-chlorovinyl compounds (Y=F, X¹=Cl, X²=H) can be prepared as follows:

Scheme 10

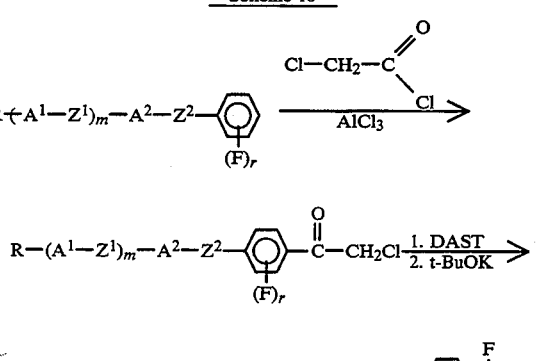

Scheme 11

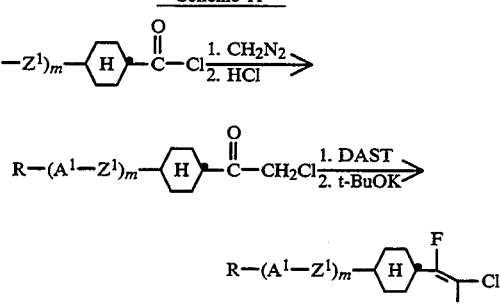

The dichlorofluorovinyl compounds (Y=F, X¹=X²=Cl) can be prepared as follows:

Scheme 12

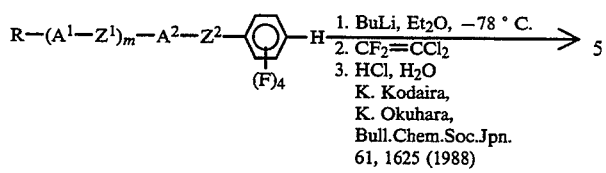

The 1,2-difluorovinyl compounds (Y=F, X¹=F, X²=F or SF₅) can be prepared as follows:

Scheme 13

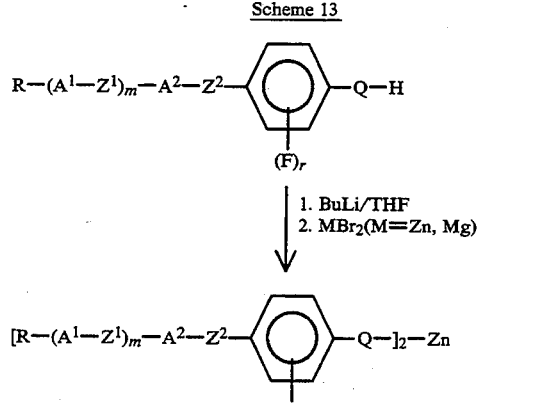

Scheme 14

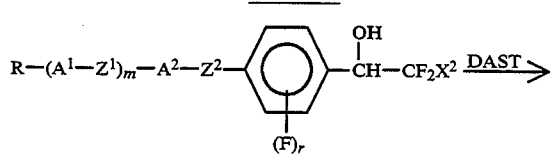

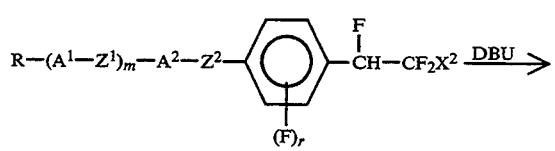

The 1,1,1,2,3-pentafluorovinyl ethers (Q=O, Y=F, X¹=F, X²=CF₃) can be prepared in accordance with the schemes below:

Scheme 15

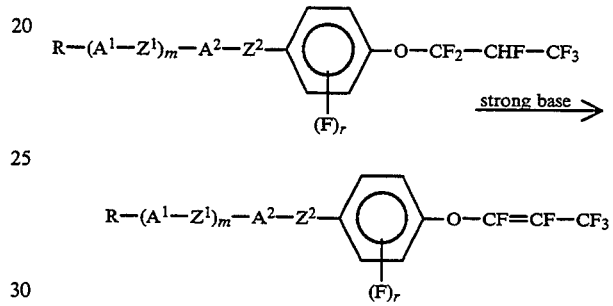

Suitable strong bases are potassium t-butylate, lithium diisopropylamide, n-butyllithium/potassium t-butylate and t-butyllithium. Preference is given to potassium t-butylate in a polar aprotic solvent, such as dimethyl sulfoxide.

Scheme 16

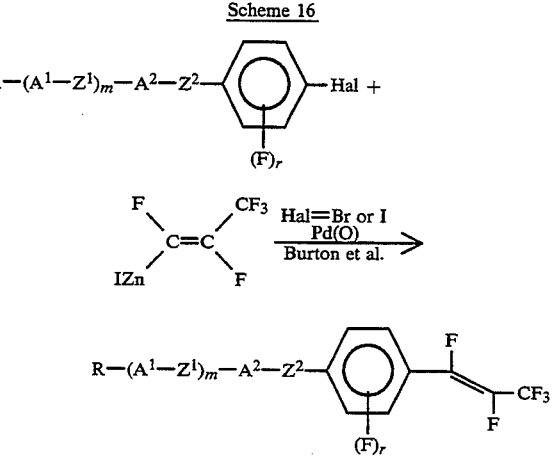

The 1,2-dichlorovinyl compounds (Y=X¹=Cl, X²=H) are prepared as follows:

Scheme 17

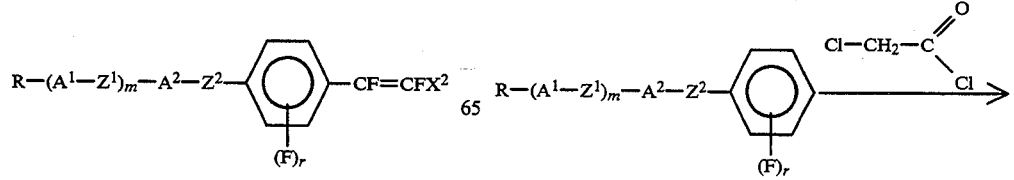

-continued
Scheme 17
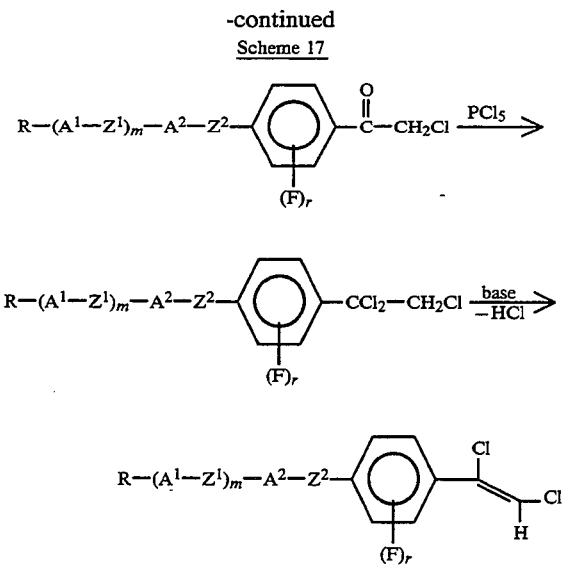
The 1,1-dichlorovinyl compound (Y=H, $X^1=X^2=Cl$) can be prepared as described in Scheme 18.
Scheme 18
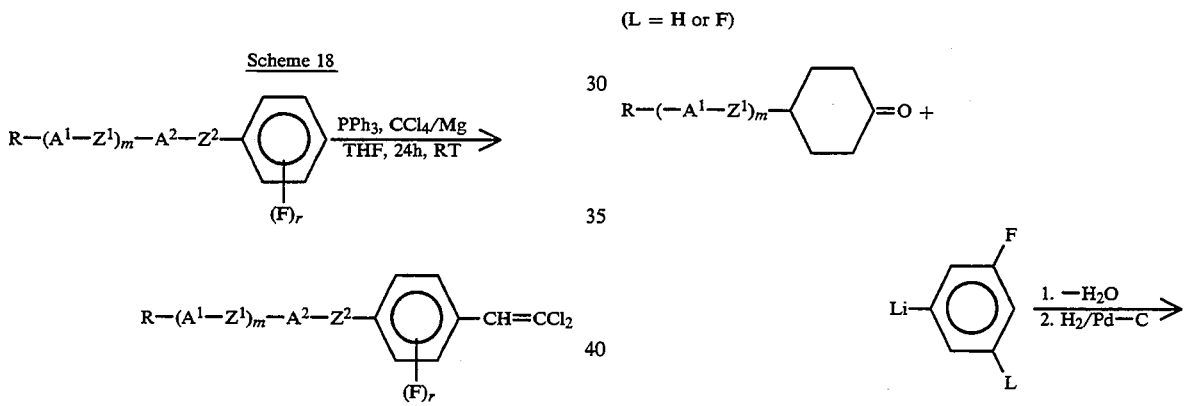
The synthesis of some particularly preferred compounds is given in greater detail below:
Scheme 19
(L=H or F)
-continued
Scheme 19
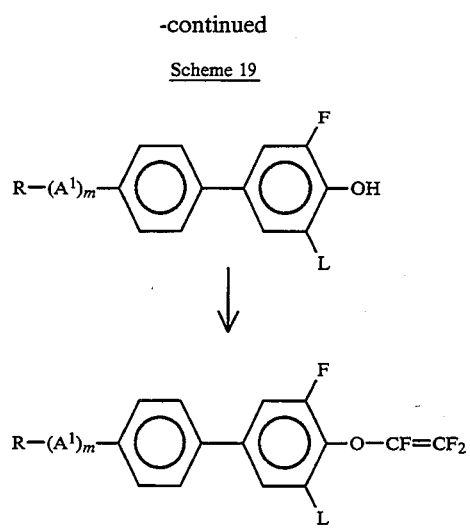
Scheme 20
(L = H or F)
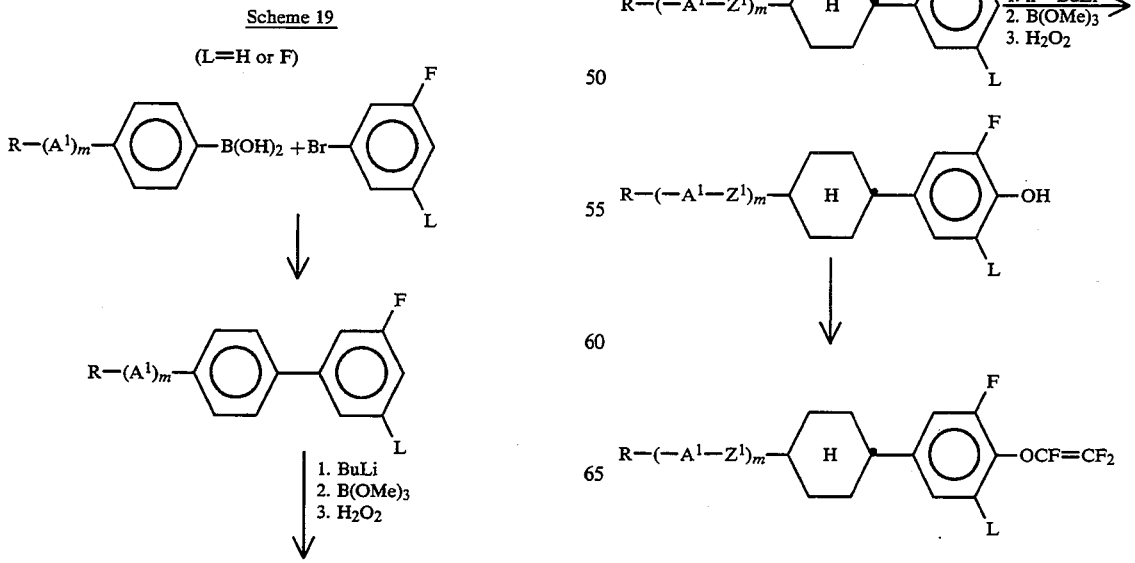

Scheme 21
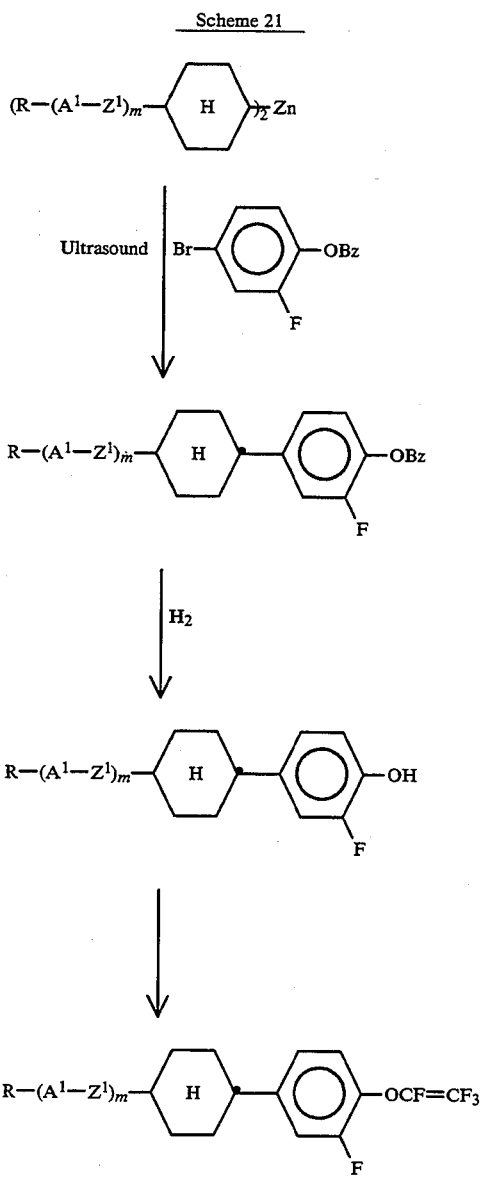
In Schemes 19, 20 and 21, m is preferably 0 or 1, and -A$^1$-Z$^1$ is preferably
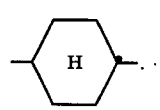
Scheme 22
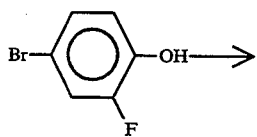
-continued
Scheme 22
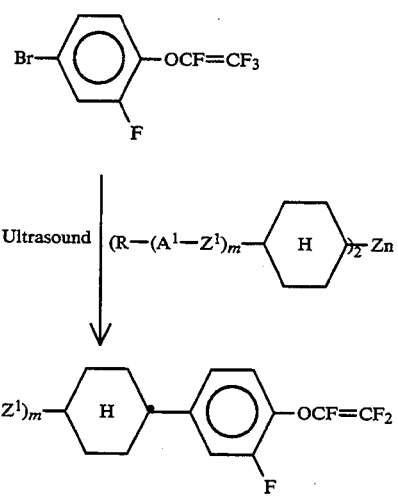
Scheme 23
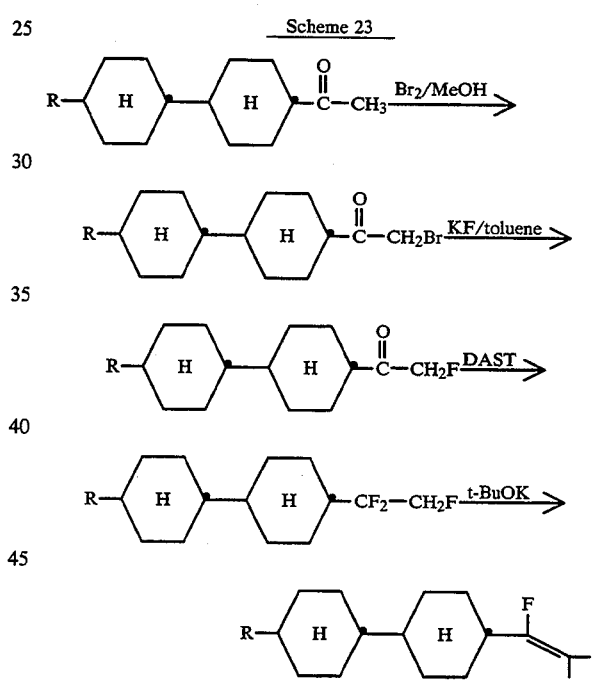
Scheme 24
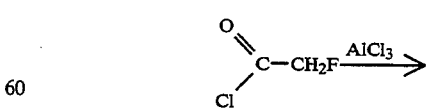
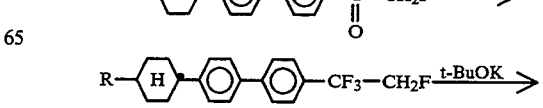

-continued
Scheme 24
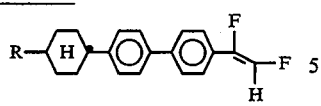
Scheme 25
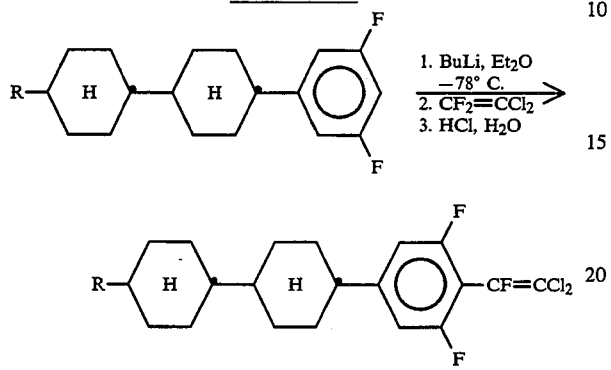
Scheme 26
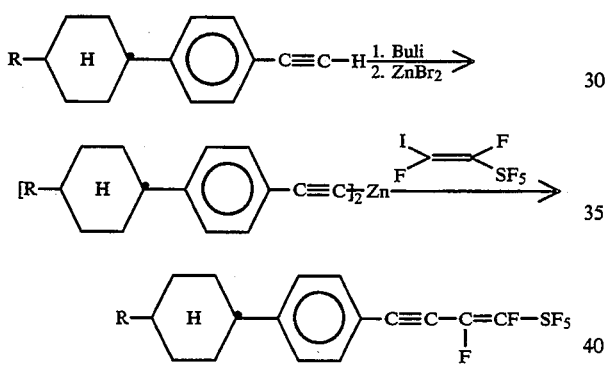
Scheme 27
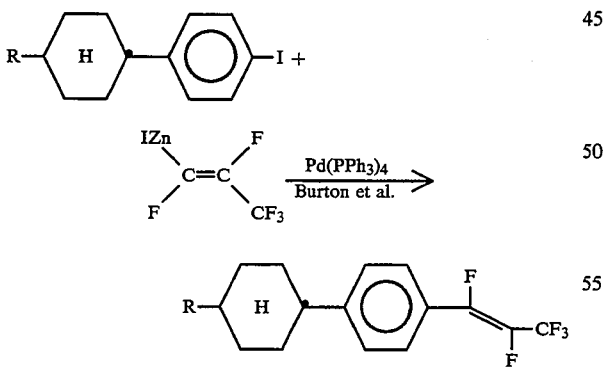
Scheme 28
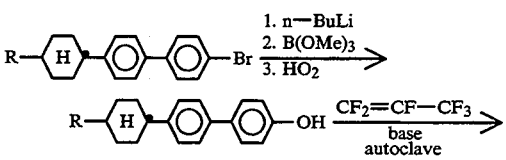
-continued
Scheme 28
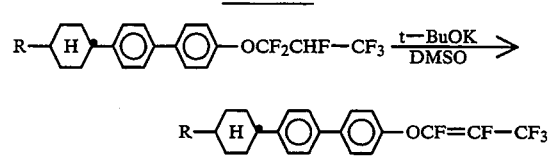
Scheme 29
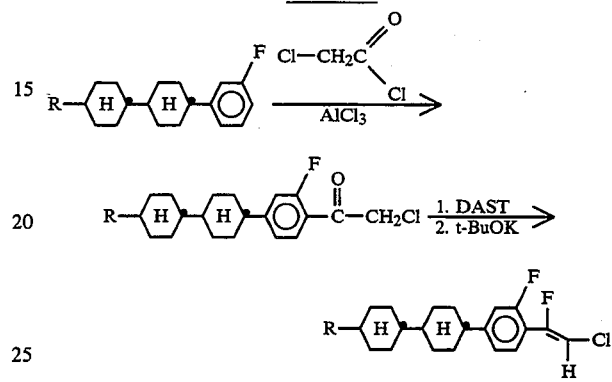
Scheme 30
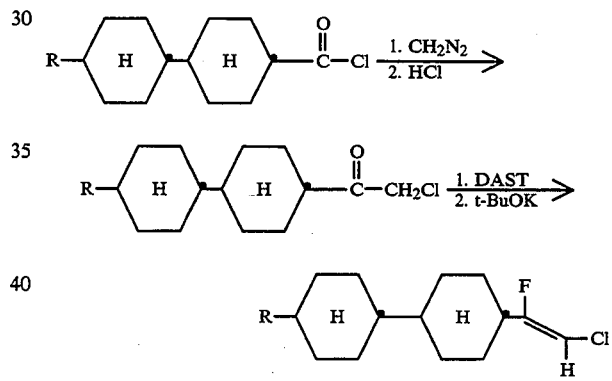
Scheme 31
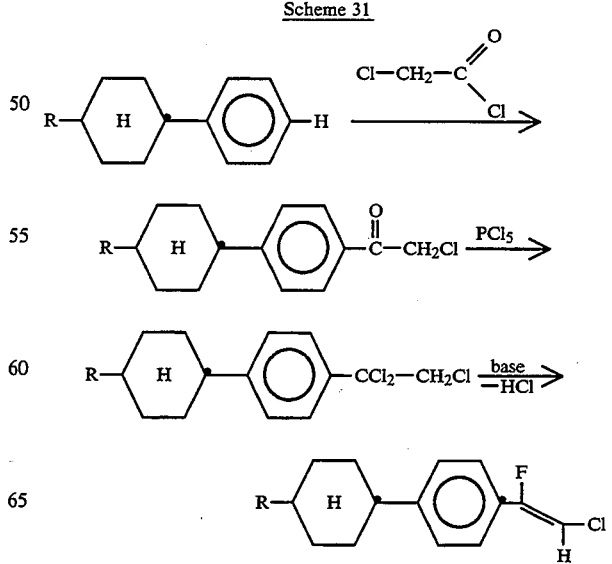

Scheme 32

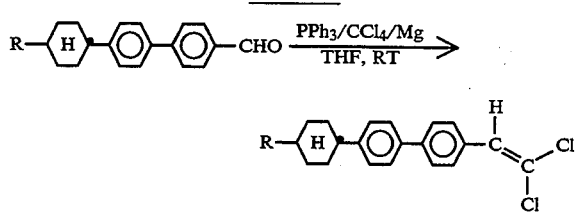

Scheme 33

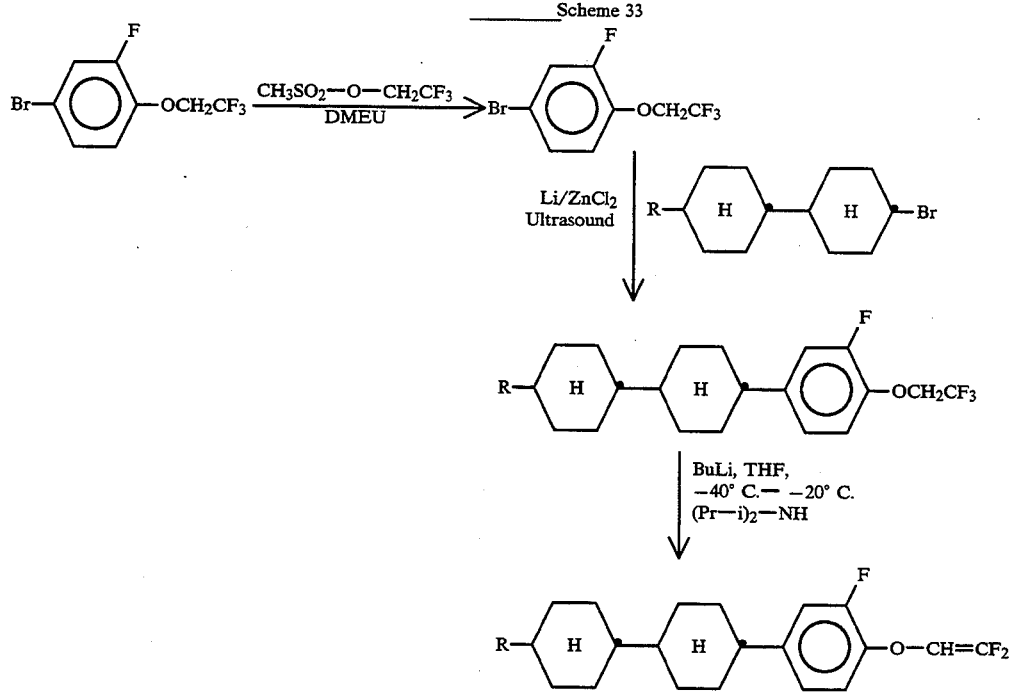

Scheme 34

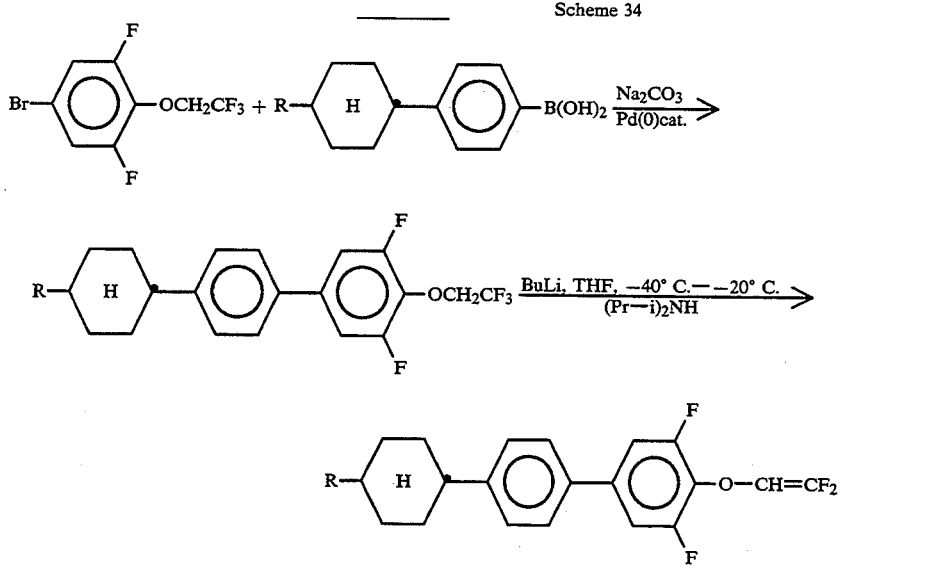

besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexyl- The liquid-crystalline media according to the invention preferably contain 2 to 40, in particular 4 to 30, components as further constituents besides one or more compounds according to the invention. These media very-particularly preferably contain 7 to 25 components cyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-bis-cyclohexylbenzenes, 4,4′-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes optionally halogenated stilbenes, benzyl phenyl ethers, tolans and substituted cinnamic acids. The 1,4-phenylene groups in these compounds may also be fluorinated.

The most important compounds suitable as further constituents of media according to the invention can be characterized by the formulae 1, 2, 3, 4 and 5:

$$R'-L-E-R'' \qquad 1$$

$$R'-L-COO-E-R'' \qquad 2$$

$$R'-L-OOC-E-R'' \qquad 3$$

$$R'-L-CH_2CH_2-E-R'' \qquad 4$$

$$R'-L-C\equiv C-E-R'' \qquad 5$$

In the formulae 1, 2, 3, 4 and 5, L and E, which may be identical or different, are in each case, independently of one another, a bivalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe is unsubstituted or fluorine-substituted 1,4-phenylene, Cyc is trans-1,4-cyclohexylene or 1,4-cyclohexylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The media according to the invention preferably contain one or more components selected from the compounds of the formulae 1, 2, 3, 4 and 5 in which L and E are selected from the group comprising Cyc, Phe and Pyr and simultaneously one or more components selected from the compounds of the formulae 1, 2, 3, 4 and 5 in which one of the radicals L and E is selected from the group comprising Cyc, Phe and Pyr and the other radical is selected from the group comprising -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group comprising -Phe-Cyc-, -Cyc-Cyc-, -G-Phe- and -G-Cyc-.

In a smaller sub-group of the compounds of the formulae 1, 2, 3, 4 and 5, R′ and R″ are in each case, independently of one another, alkyl, alkenyl, alkoxy, alkoxyalkyl, alkenyloxy or alkanoyloxy having up to 8 carbon atoms. This smaller sub-group is called group A below, and the compounds are labeled with the sub-formulae 1a, 2a, 3a, 4a and 5a. In most of these compounds, R′ and R″ are different from one another, one of these radicals usually being alkyl, alkenyl, alkoxy or alkoxyalkyl.

In another smaller sub-group of the compounds of the formulae 1, 2, 3, 4 and 5 which is known as group B, R″ is —F, —Cl, —NCS or —(O)$_i$CH$_{3-(k+1)}$F$_k$Cl$_l$, where i is 0 or 1, and k+l is 1, 2 or 3; the compounds in which R″ has this meaning are labeled with the sub-formulae 1b, 2b, 3b, 4b and 5b. Particular preference is given to those compounds of the sub-formulae 1b, 2b, 3b, 4b and 5b in which R″ is —F, —Cl, —NCS, —CF$_3$, —OCHF$_2$ or —OCF$_3$.

In the compounds of the sub-formulae 1b, 2b, 3b, 4b and 5b, R′ is as defined for the compounds of the sub-formulae 1a-5a and is preferably alkyl, alkenyl, alkoxy or alkoxyalkyl.

In a further smaller sub-group of the compounds of the formulae 1, 2, 3, 4 and 5, R″ is —CN; this sub-group is known as group C below, and the compounds of this sub-group are correspondingly described by subformulae 1c, 2c, 3c, 4c and 5c. In the compounds of the sub-formulae 1c, 2c, 3c, 4c and 5c, R′ is as defined for the compounds of the sub-formulae 1a-5a and is preferably alkyl, alkoxy or alkenyl.

In addition to the preferred compounds of groups A, B and C, other compounds of the formulae 1, 2, 3, 4 and 5 having other variants of the proposed substituents are also customary. All these substances can be obtained by methods which are known from the literature or analogously thereto.

Besides compounds of the formula I according to the invention, the media according to the invention preferably contain one or more compounds selected from group A and/or group B and/or group C. The proportions by weight of the compounds from these groups in the media according to the invention are preferably Group A: 0 to 90%, preferably 20 to 90%, in particular 30 to 90%

Group B: 0 to 80%, preferably 10 to 80%, in particular 10 to 65%

Group C: 0 to 80%, preferably .5 to 80%, in particular 5 to 50%, the sum of the proportions by weight of the group A and/or B and/or C compounds present in the particular media according to the invention preferably being 5%-90% and in particular 10% to 90%.

The media according to the invention preferably contain 1 to 40%, particularly preferably 5 to 30%, of compounds according to the invention. Further preferred media are those which contain more than 40%, in particular 45 to 90%, of compounds according to the invention. The media preferably contain three, four or five compounds according to the invention.

The media according to the invention are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of colored guest-host systems, or substances can be added to modify the dielectric anisotropy, the viscosity and/or the orientation of the nematic phases.

In the present application and in the examples below, the structures of the liquid-crystal compounds are indicated by acronyms, the transformation into chemical formulae taking place as in Tables A and B below. All the radicals $C_nH_{2n+1}$ and $C_mH_{2m+1}$ are straight-chain alkyl radicals containing n or m carbon atoms. The coding in Table B requires no further explanation. In Table A, only the acronym for the parent structure is given. In individual cases, a code follows for the substituents $R^1$, $R^2$, $L^1$ and $L^2$, separated from the acronym for the parent structure by a hyphen:

| Code for $R^1$, $R^2$, $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | H | F |
| nF | $C_nH_{2n+1}$ | F | H | H |
| nOF | $OC_nH_{2n+1}$ | F | H | H |
| nCl | $C_nH_{2n+1}$ | Cl | H | H |
| nF.F | $C_nH_{2n+1}$ | F | H | F |
| nOmFF | $C_nH_{2n+1}$ | $OC_mH_{2m+1}$ | F | F |
| nmF | $C_nH_{2n+1}$ | $C_mH_{2m+1}$ | F | H |
| nCF3 | $C_nH_{2n+1}$ | $CF_3$ | H | H |
| nOCF3 | $C_nH_{2n+1}$ | $OCF_3$ | H | H |
| nOCF2 | $C_nH_{2n+1}$ | $OCHF_2$ | H | H |
| nS | $C_nH_{2n+1}$ | NCS | H | H |
| rVsN | $C_rH_{2r+1}-CH=CH-C_sH_{2s}-$ | CN | H | H |
| rEsN | $C_rH_{2r+1}-O-C_sH_{2s}-$ | CN | H | H |
| nNF | $C_nH_{2n+1}$ | CN | F | H |
| nAm | $C_nH_{2n+1}$ | $COOC_mH_{2m+1}$ | H | H |

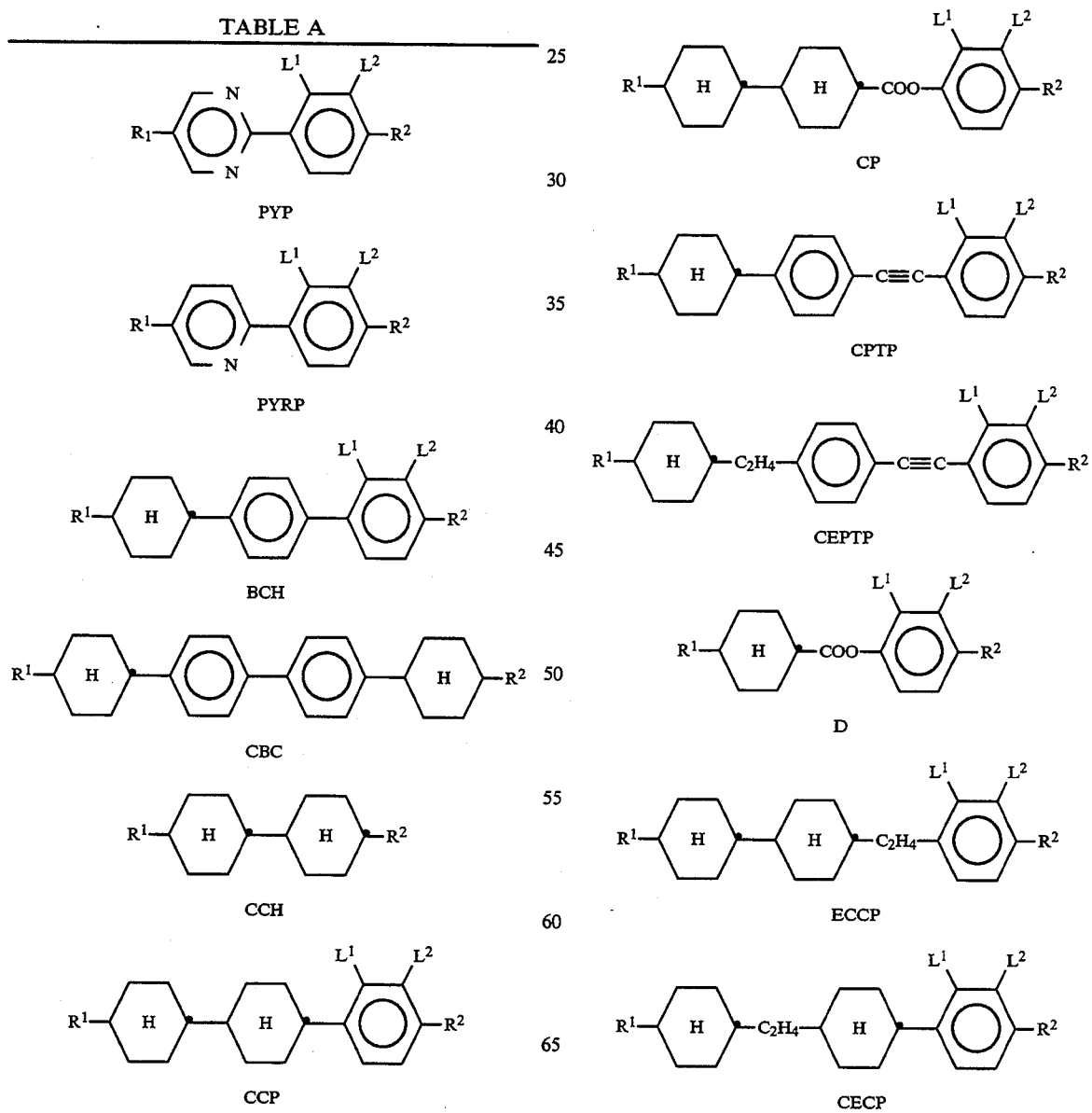

TABLE A

PYP

PYRP

BCH

CBC

CCH

CCP

CP

CPTP

CEPTP

D

ECCP

CECP

TABLE A-continued
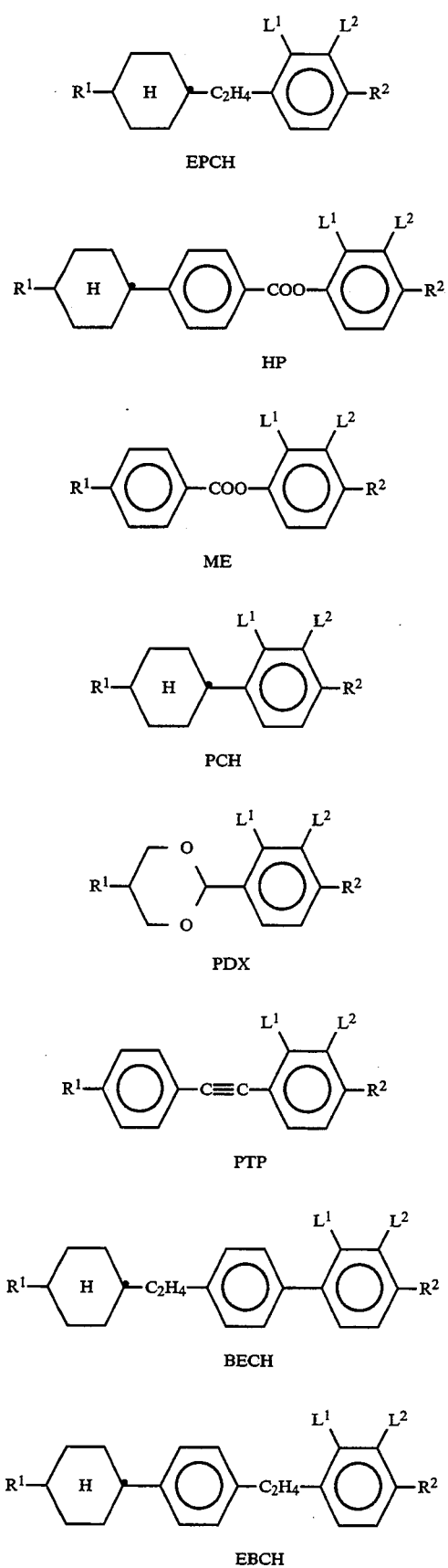
EPCH
HP
ME
PCH
PDX
PTP
BECH
EBCH
TABLE A-continued
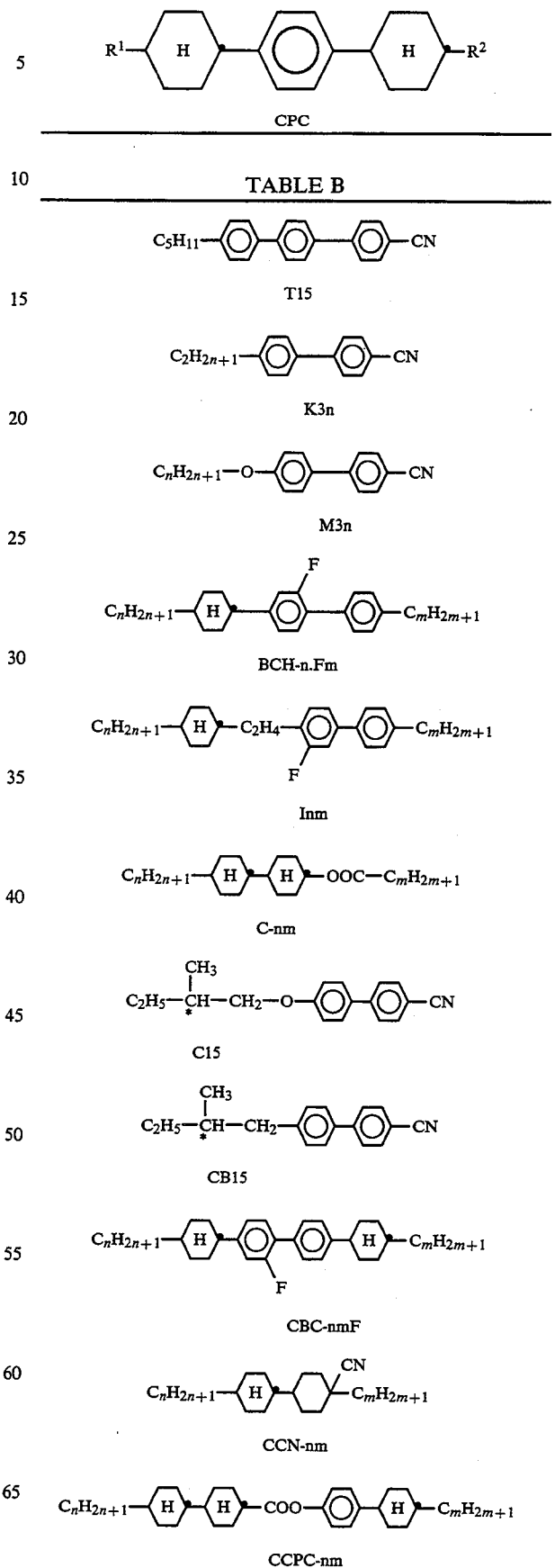
CPC
TABLE B
T15
K3n
M3n
BCH-n.Fm
Inm
C-nm
C15
CB15
CBC-nmF
CCN-nm
CCPC-nm

TABLE B-continued

CH-nm: $C_nH_{2n+1}$—[H]—[H]—COO—[H]—$C_mH_{2m+1}$

HD-nm: $C_nH_{2n+1}$—[H]—[◯]—OOC—[H]—$C_mH_{2m+1}$

HH-nm: $C_nH_{2n+1}$—[H]—[◯]—COO—[H]—$C_mH_{2n+1}$

NCB-nm: $C_nH_{2n+1}$—[◯]—[◯]—[H(CN)]—$C_mH_{2m+1}$

OS-nm: $C_nH_{2n+1}$—[H]—COO—[H]—$C_mH_{2m+1}$

CHE: $C_2H_5$—[H]—COO—[◯]—[◯]—CN

ECBC-nm: $C_nH_{2n+1}$—[H]—$C_2H_4$—[◯]—[◯]—[H]—$C_mH_{2m+1}$

ECCH-nm: $C_nH_{2n+1}$—[H]—$C_2H_4$—[H]—$C_mH_{2m+1}$

CCH-n1Em: $C_nH_{2n+1}$—[H]—[H]—$CH_2O$—$C_mH_{2m+1}$

T-nFn: $C_nH_{2n+1}$—[◯]—[◯(F)]—[◯]—CN

ECCH-nm: $C_nH_{2n+1}$—[H]—$C_2H_4$—[H]—$C_mH_{2m+1}$

CCH-n1Em: $C_nH_{2n+1}$—[H]—[H]—$CH_2OC_mH_{2m+1}$

T-nFN: $C_nH_{2n+1}$—[◯]—[◯(F)]—[◯]—CN

TABLE B-continued

CCH-n2CF3: $C_nH_{2n+1}$—[H]—[H]—$CGH_2CH_2CF_3$

CCP-nF.F.F: $C_nH_{2n+1}$—[H]—[H]—[◯(F,F,F)]

BCH-nF.F.F: $C_nH_{2n+1}$—[H]—[◯]—[◯(F,F,F)]

The examples below are intended to illustrate the invention without representing a limitation. Above and below, percentage data are percent by weight. All temperatures are given in degrees Celsius. m.p. denotes melting point, c.p.=clearing point. Furthermore, C=crystalline stage, N=nematics phase, S=smectic phase and I=isotropic phase. The data between these symbols represent the transition temperatures. An denotes optical anisotropy (589 nm, 20° C.), and the viscosity (mm2/sec) was determined at 20° C.

"Customary work-up" means that water is added if necessary, the mixture is extracted with dichloromethane, diethyl ether or toluene, the organic phase is separated off, dried and evaporated, and the product is purified by distillation under reduced pressure or crystallization and/or chromatography. The following abbreviations are used:

| | |
|---|---|
| DAST | diethylaminosulfur trifluoride |
| DCC | dicyclohexylcarbodiimide |
| DDQ | dichlorodicyanobenzoquinone |
| DIBALH | diisobutylaluminum hydride |
| POT | potassium tertiary-butanolate |
| PdCl2 dppf | 1,1'-bis(diphenylphosphino)ferrocene-palladium(II) chloride |
| THF | tetrahydrofuran |
| pTSOH | p-toluenesulfonic acid |
| TMEDA | tetramethylethylenediamine |

EXAMPLE 1

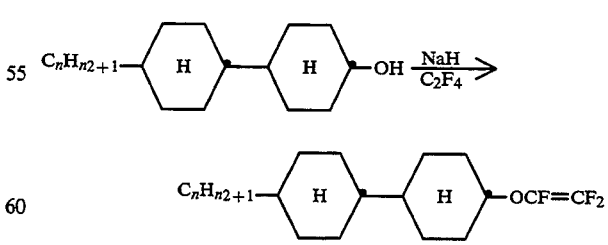

1.2 g of sodium hydride are added under an atmosphere of dry nitrogen to a solution of 12.5 g of the known compound 5-pentyl-trans,trans-bicyclo-1-hexanol and 0.5 g of hydroquinone in 50 ml of 1,4-dioxane in an autoclave with a capacity of 200 ml. The autoclave is sealed, and its contents are stirred with a magnetic stirrer, first for 2 hours at room temperature and then for 2 hours at 120° C. The pressure vessel is then cooled, first in an ice bath and then by means of liquid nitrogen. After the autoclave is evacuated to a pressure of <0.1 mmHg, 15 g of tetrafluoroethene are condensed in with exclusion of air. The mixture is stirred at from 50° to 60° C. for 20 hours. The mixture is cooled to 0° C., and the excess tetrafluoroethene is released. The reaction mixture is introduced into 20 ml of water. The mixture is extracted 3 times with 100 ml of diethyl ether in each case, and the combined organic phases are dried using $Na_2SO_4$ and evaporated. The residue is extracted by stirring at room temperature with 100 ml of toluene, leaving the majority of the starting alcohol. The solution is evaporated, and the residue is subjected to separation by column chromatography (silica gel/petroleum ether). Recrystallization of the main fraction from a mixture of equal parts by volume of toluene and ethanol gives 5-pentyl-1-trifluorovinyloxy-trans,trans-bicyclohexane.

The compounds

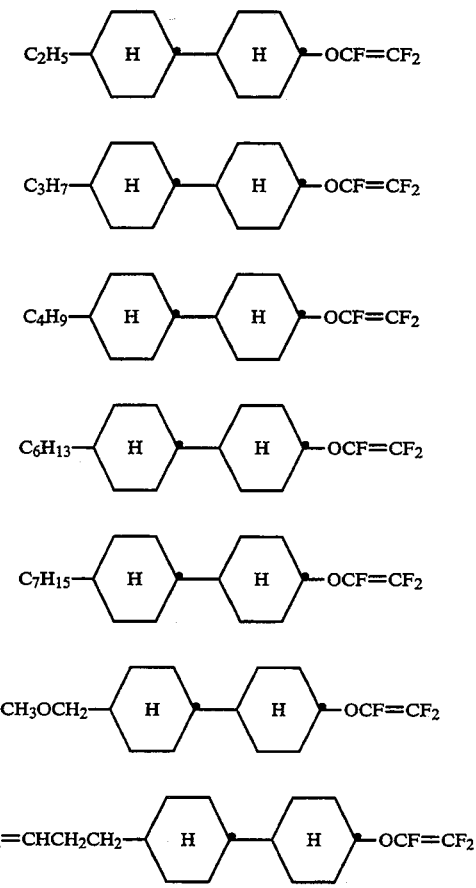

are prepared analogously.

EXAMPLE 2

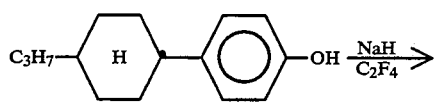

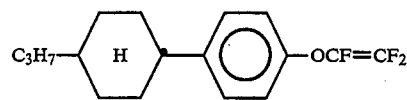

A solution of 10 g of p-(trans-4-n-propylcyclohexyl)-phenol in a mixture of 40 ml of benzene and 10 ml of tetrahydrofuran is reacted with sodium hydride analogously to Example 1. After tetrafluoroethene has been condensed in, the mixture is heated at 140° C. for about 20 hours and treated as described in Example 1. p-(trans-4-n-propylcyclohexyl)trifluorovinyloxybenzene is obtained.

The following are prepared analogously:
p-(trans-4-ethylcyclohexyl)trifluorovinyloxybenzene
p-(trans-4-n-butylcyclohexyl)trifluorovinyloxybenzene
p-(trans-4-n-pentylcyclohexyl)trifluorovinyloxybenzene
p-(trans-4-n-hexylcyclohexyl)trifluorovinyloxybenzene
p-(trans-4-n-heptylcyclohexyl)trifluorovinyloxybenzene
p-(trans-4-n-ethylcyclohexylcyclohexyl)trifluorovinyloxybenzene
p-(trans-4-n-propylcyclohexylcyclohexyl)trifluorovinyloxybenzene
p-(trans-4-n-butylcyclohexylcyclohexyl)trifluorovinyloxybenzene
p-(trans-4-n-pentylcyclohexylcyclohexyl)trifluorovinyloxybenzene, C 47 $S_B$ 103 I
p-(trans-4-n-hexylcyclohexylcyclohexyl)trifluorovinyloxybenzene
p-(trans-4-n-heptylcyclohexylcyclohexyl)trifluorovinyloxybenzene
p-(5-ethylpyrimidin-2-yl)trifluorovinyloxybenzene
p-(5-n-propylpyrimidin-2-yl)trifluorovinyloxybenzene
p-(5-n-butylpyrimidin-2-yl)trifluorovinyloxybenzene
p-(5-n-pentylpyrimidin-2-yl)trifluorovinyloxybenzene
p-(5-n-hexylpyrimidin-2-yl)trifluorovinyloxybenzene
p-(5-n-heptylpyrimidin-2-yl)trifluorovinyloxybenzene

EXAMPLE 3

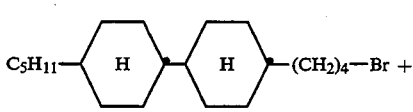

I

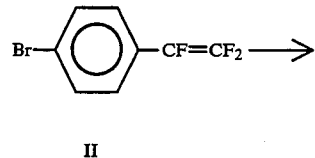

II

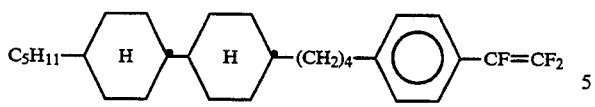

III 37.1 g of I (0.1 mol) are introduced into 150 ml of a solvent mixture of THF/toluene (1:4 volume ratio), and then 11.5 g of anhydrous zinc bromide followed by 1.4 g of lithium granules are added. The mixture is treated with ultrasound for 4 hours at between 0° and 10° C. under argon and with stirring in order to convert I into the corresponding dialkylzinc compound. The organozinc compound is treated with 21.1 g of II (0.1 mol) and 1.5 g (2 mol %) of 1,1'-bis(diphenylphosphino)ferrocenepalladium(II) dichloride (PdCl₂ dppf), the ultrasound bath and the cooling are removed, and the mixture is stirred at room temperature for 24 hours. It is decomposed with 100 ml of saturated NH₄Cl solution, the organic phase is separated off, and the aqueous phase is extracted twice with toluene. The combined organic extracts are dried, evaporated and chromatographed on silica gel using hexane to give III. (I can be prepared by chain lengthening of

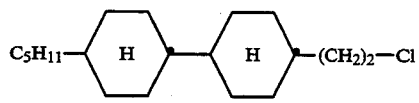

by means of ethyl malonate.) The alkyl bromides listed below can be reacted with II analogously to I:

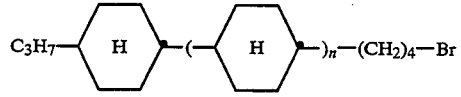

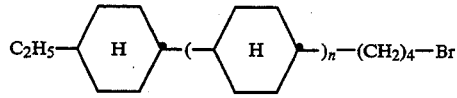

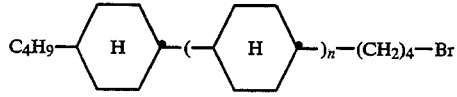

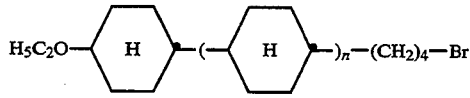

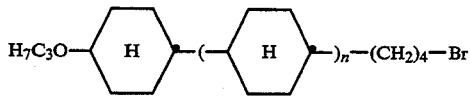

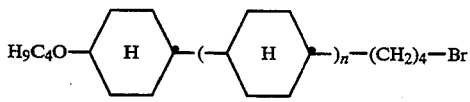

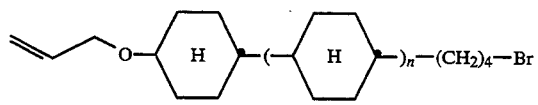

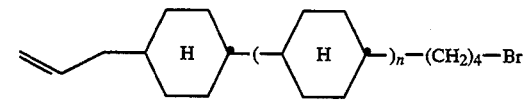

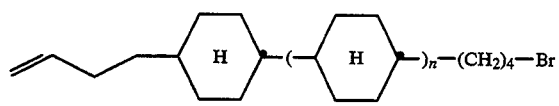

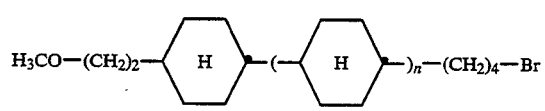

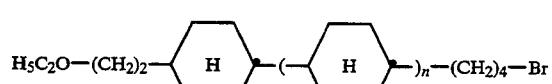

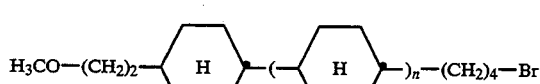

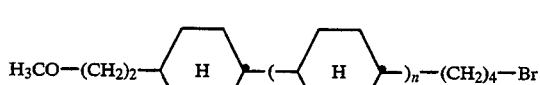

n=0 and 1

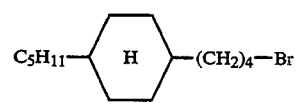

also 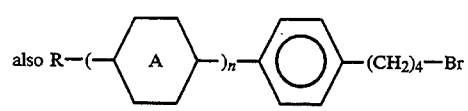

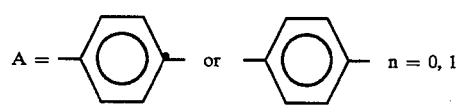  n = 0, 1

EXAMPLE 4

4-(4-Heptylcyclohexyl)-1-(1,2,3-trifluorovinyl)benzene

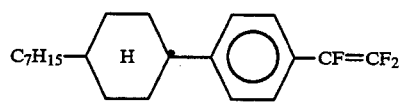

36 ml of a 15% solution of butyllithium in hexane are added dropwise at −70° to 16.87 g (50 mmol) of 1-bromo-4-(4-heptycyclohexyl)benzene in 300 ml of diethyl ether/THF 1:1. The mixture is stirred for 1 hour, and, at −70°, a vigorous stream of tetrafluoroethylene is passed through the mixture (a total of about 20 g). the mixture is warmed to room temperature, and acidified with 100 ml of 1N hydrochloric acid; the organic phase is separated off and evaporated in vacuo. The residue is distilled in vacuo (about 0.1 mmHg) at about 180°.

The following is obtained analogously:

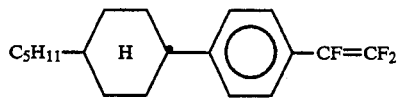

EXAMPLE 5

4-[4-(4-Propylcyclohexyl)cyclohexyl]-1-(1,2,2-trifluorovinyl)benzene

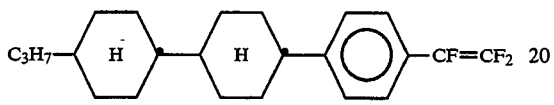

A mixture of 5.0 g (77 mmol) of zinc powder, 50 ml of THF and 13.5 g (65 mmol) of trifluoroiodoethylene is stirred overnight, initially with ice cooling, later at room temperature. 20.5 g (50 mmol) of 1-iodo-4-[4-(4-propylcyclohexyl)cyclohexyl]benzene and 1.1 g-of tetrakis(triphenylphosphine)palladium are then added.

After the mixture has been refluxed overnight, it is evaporated, and the residue is taken up in toluene and chromatographed on a silica gel column using toluene as eluent. The eluate is evaporated in vacuo, and the residue is recrystallized from hexane/ethyl acetate.

The following is obtained analogously:

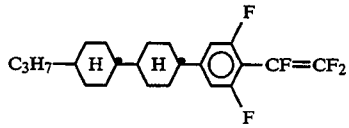

C 60 N 93 I, $\Delta n=0.065$

EXAMPLE 6

4-(4-Pentylcyclohexyl)cyclohexyl-4'-(1,2,2-trifluorovinyl))biphenyl

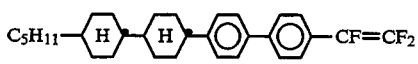

36 ml (58 mmol) of 15% solution of butyllithium in hexane are added dropwise at −20° to a solution of 5.05 g (50 mmol) of diisopropylamine in 25 ml of THF. After the mixture has been stirred at this temperature for ½ hour, a solution of 18.8 g of (4-pentylcyclohexyl)cyclohexyl-4'-(1,1,2,2-tetrafluoroethyl)biphenyl (DE-A 40 02 374) in 100 ml of THF are added dropwise at −70°. The mixture is allowed to warm slowly to room temperature, and is then refluxed for a further 10 minutes. After cooling, the mixture is acidified by means Of 1N hydrochloric acid; the organic phase is separated off, washed twice with 50 ml water and then evaporated in vacuo. The residue is chromatographed on a silica gel column using toluene as eluent, the eluate is evaporated in vacuo, and the residue is recrystallized from cyclohexane/ethyl acetate.

EXAMPLE 7

4-(4-Pentylcyclohexyl)cyclohexyl)-1,2,2,-trifluorovinyl ether

A procedure analogous to that in Example 6 is carried out using 16.0 g ! (50 mmol) of (4-pentylcyclohexyl)cyclohexyl 1,1,2,2-tetrafluoroethyl ether (purification by low-temperature crystallization from pentane).

The following compounds of the formula

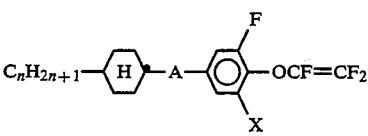

are prepared analogously:

| n | A | X |
|---|---|---|
| 2 | Single bond | H |
| 3 | Single bond | H |
| 4 | Single bond | H |
| 5 | Single bond | H |
| 2 | Single bond | F |
| 3 | Single bond | F |
| 4 | Single bond | F |
| 5 | Single bond | F |
| 2 | phenylene | H |
| 3 | phenylene | H |
| 4 | phenylene | H |
| 5 | phenylene | H |
| 2 | phenylene | F |
| 3 | phenylene | F |
| 4 | phenylene | F |

-continued

| n | A | X |
|---|---|---|
| 5 |  | F |
| 2 | 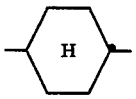 | H |
| 3 | 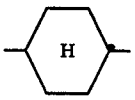 | H |
| 4 |  | H |
| 5 |  | H |
| 2 |  | F |
| 3 |  | F |
| 4 |  | F |
| 5 | 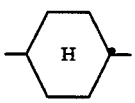 | F |

EXAMPLE 8

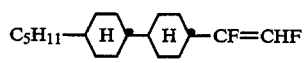

Step 8.1

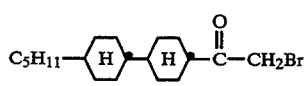

0.5 mol of bromine is slowly added dropwise at from 0° to 5° C. to 0.5 mol of n-pentylcyclohexylcyclohexyl methyl ketone dissolved in 300 ml of absolute methanol. After about 1 hour, 150 ml of water are added to the solution, and the mixture is subsequently stirred overnight. A further 450 ml of water are added, and the mixture is subjected to customary work-up.

Step 8.2

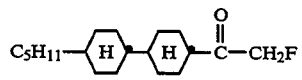

0.05 mol of anhydrous potassium fluoride is added to 0.45 mmol of 18-crown-6 in 25 ml of toluene. The mixture is stirred at room temperature for 15 minutes, 0.025 mol of the brominated ketone from Step 8.1 is added, and the mixture is stirred at 80° C. for 24 hours. The mixture is subsequently subjected to customary work-up.

Step 8.3

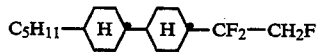

17 mmol of the fluoromethyl ketone (Step 8.2) in 10 ml of absolute toluene are added to 26 mmol of DAST under a nitrogen atmosphere. The mixture is subsequently stirred at 50° C. for 17 hours. The mixture is then cooled to 0° C., water is carefully added, and the mixture washed with sodium hydrogen carbonate solution until neutral. The mixture is subsequently subjected to customary work-up.

Step 8.4

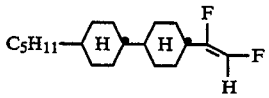

25 mmol of the trifluoro compound (Step 8.3) are added to a solution of 50 mmol of potassium tert. butylate in 20 ml of tert.-butanol, and the mixture is warmed at 100° C. for 18 hours. After cooling, the mixture is poured into water and subjected to customary work-up. C 25 N 73.8 I; Δn=+0.039

The following compounds of the formula

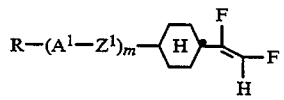

are prepared analogously:

| R | $-(A^1-Z^1)_m-$ |
|---|---|
| $C_2H_5$ |  |

-continued
| R | $-(A^1-Z^1)_m-$ | |
|---|---|---|
| n-C₃H₇ | 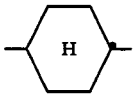 | C 19 N 54 I; Δn = +0.049 |
| n-C₄H₉ | 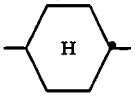 | C 15 N 54.2 I; Δn = +0.041 |
| n-C₇H₁₅ | 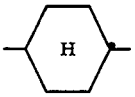 | |
| CH₃OCH₂ |  | |
| n-C₃H₇ |  | |
| n-C₅H₁₁ |  | |
| CH₂=CHCH₂CH₂ |  | |
| C₂H₅ | 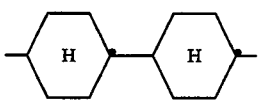 | |
| n-C₃H₇ | 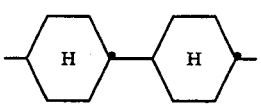 | |
| n-C₅H₁₁ | 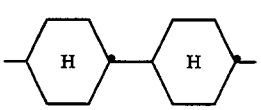 | |
| C₂H₅ | 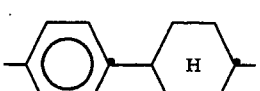 | |
| n-C₄H₉ | 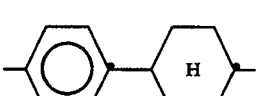 | |
| n-C₅H₁₁ | 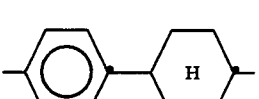 | |

-continued
| R | $-(A^1-Z^1)_m-$ |
|---|---|
| $C_2H_5$ | 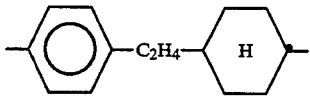 |
| n-$C_3H_7$ | 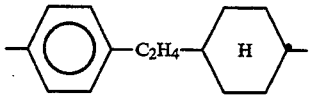 |
| n-$C_5H_{11}O$ | 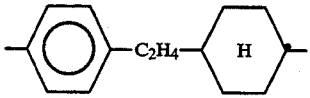 |
| $C_2H_5$ | 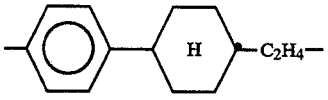 |
| n-$C_3H_7$ | 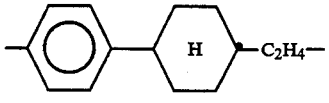 |
| n-$C_5H_{11}$ | 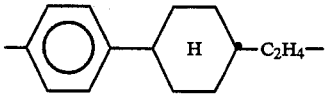 |
| n-$C_3H_7$ | 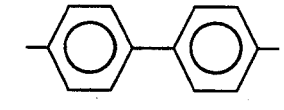 |
| n-$C_5H_{11}$ | 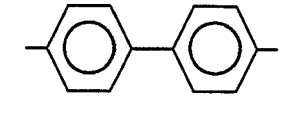 |
| $CH_3CH_2O$ | 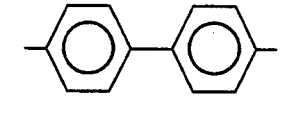 |
| n-$C_3H_7$ | 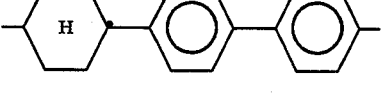 |
| n-$C_5H_{11}$ | 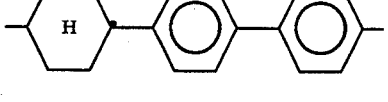 |
| n-$C_5H_{11}O$ | 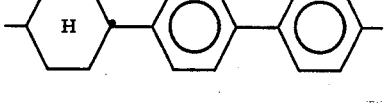 |
| n-$C_3H_7$ | 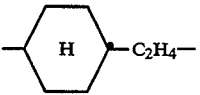 |

-continued

| R | $-(A^1-Z^1)_m-$ |
|---|---|
| n-C$_5$H$_{11}$ | 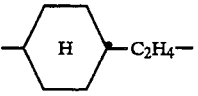 |
| CH$_3$OCH$_2$ | 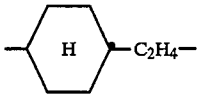 |
| CH$_3$OCH$_2$ | 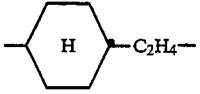 |
| n-C$_3$H$_7$ | 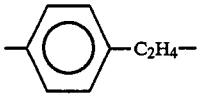 |
| n-C$_5$H$_{11}$ | 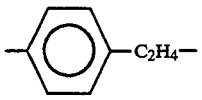 |
| n-C$_6$H$_{13}$ | 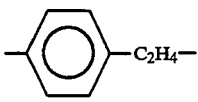 |
| n-C$_3$H$_7$ | 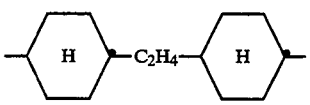 |
| n-C$_5$H$_{11}$ | 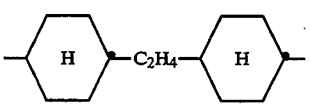 |
| n-C$_3$H$_7$ | 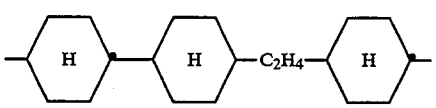 |
| n-C$_5$H$_{11}$ | 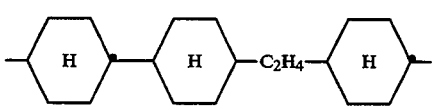 |

EXAMPLE 9

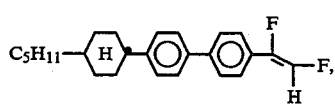

0.52 mol of fluoroacetyl chloride is added dropwise at 0° C. with stirring to 0.6 mol of powdered aluminum chloride and 200 ml of dichloromethane. 0.5 mol of n-pentylcyclohexylbiphenyl is subsequently added to the mixture with cooling. The mixture is then stirred for a further hour and left to stand overnight. It is poured onto ice and subjected to customary work-up. The fluorinated ketone obtained is reacted, analogously to 8.3 and 8.4, first with DAST, and then with potassium tert.-butylate to give the difluorovinyl compound.

The following compounds of the formula

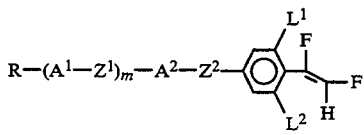

are prepared analogously.

| R | −(A¹−Z¹)$_m$−A²−Z²− | L¹ | L² | |
|---|---|---|---|---|
| n-C$_3$H$_7$ |  | H | H | |
| n-C$_3$H$_7$ | 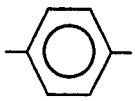 | H | F | |
| n-C$_3$H$_7$ | 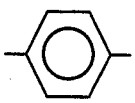 | F | F | |
| n-C$_5$H$_{11}$ | 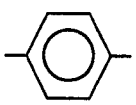 | H | H | |
| n-C$_5$H$_{11}$ | 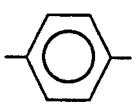 | H | F | |
| n-C$_5$H$_{11}$ | 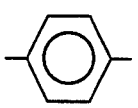 | F | F | |
| CH$_3$CH$_2$O | 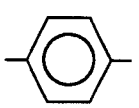 | H | F | |
| CH$_2$=CHCH$_2$CH$_2$ | 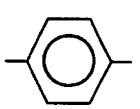 | F | F | |
| n-C$_3$H$_7$ | 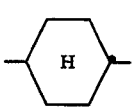 | H | H | |
| n-C$_3$H$_7$ | 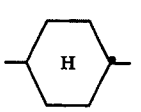 | H | F | |
| n-C$_3$H$_7$ | 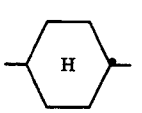 | F | F | |
| n-C$_5$H$_{11}$ | 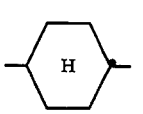 | H | H | C 30 N 61.9 I |
| n-C$_5$H$_{11}$ | 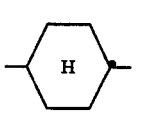 | H | F | |

-continued

| R | —(A¹—Z¹)ₘ—A²—Z²— | L¹ | L² |
|---|---|---|---|
| n-C₅H₁₁ | —[H]— | F | F  C 26 N 32 I |
| n-C₂H₅ | —[H]—[H]— | H | H |
| n-C₂H₅ | —[H]—[H]— | H | F |
| n-C₂H₅ | —[H]—[H]— | F | F |
| n-C₃H₇ | —[H]—[H]— | H | H |
| n-C₃H₇ | —[H]—[H]— | H | F |
| n-C₃H₇ | —[H]—[H]— | F | F |
| n-C₅H₁₁ | —[H]—[H]— | H | H |
| n-C₅H₁₁ | —[H]—[H]— | H | F |
| n-C₅H₁₁ | —[H]—[H]— | F | F |
| CH₂=CHCH₂CH₂ | —[H]—[H]— | H | H |
| n-C₃H₇ | —[H]—[H]—C₂H₄— | H | H |
| n-C₃H₇ | —[H]—[H]—C₂H₄— | H | F |

-continued
| R | −(A¹−Z¹)ₘ−A²−Z²− | L¹ | L² |
|---|---|---|---|
| n-C₃H₇ | 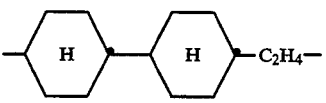 | F | F |
| n-C₅H₁₁ | 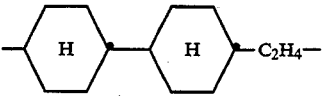 | H | H |
| n-C₅H₁₁ | 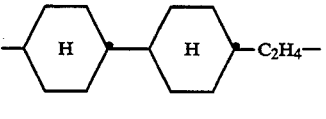 | H | F |
| n-C₅H₁₁ | 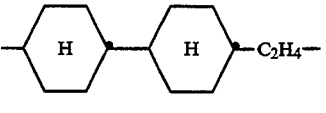 | F | F |
| n-C₃H₇ | 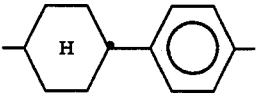 | H | H |
| n-C₃H₇ | 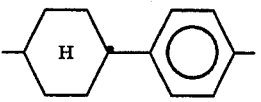 | H | F |
| n-C₃H₇ | 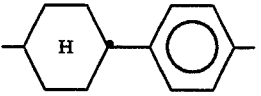 | F | F |
| n-C₅H₁₁ | 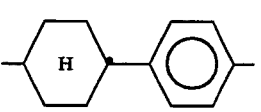 | H | F |
| n-C₅H₁₁ | 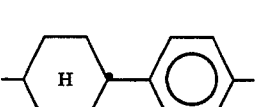 | F | F |
| n-C₃H₇ | 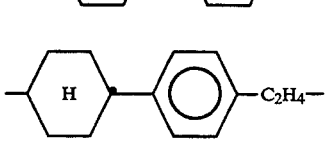 | H | H |
| n-C₃H₇ | 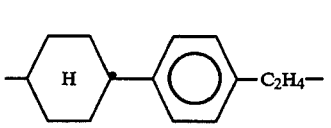 | H | F |
| n-C₃H₇ | 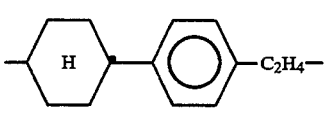 | F | F |
| n-C₅H₁₁ | 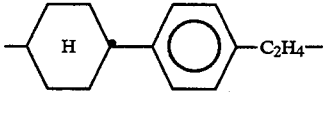 | H | H |

-continued
| R | —(A¹—Z¹)ₘ—A²—Z²— | L¹ | L² |
|---|---|---|---|
| n-C₅H₁₁ | 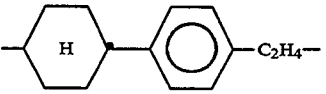 | H | F |
| n-C₅H₁₁ | 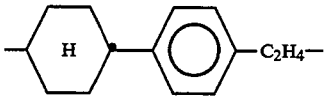 | F | F |
| n-C₃H₇ | 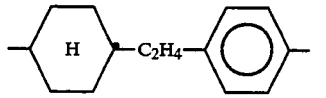 | H | H |
| n-C₃H₇ | 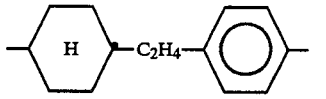 | H | F |
| n-C₃H₇ | 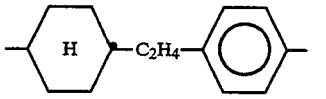 | F | F |
| n-C₅H₁₁ | 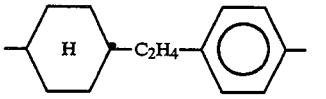 | H | H |
| n-C₅H₁₁ | 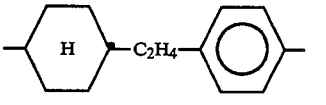 | H | F |
| n-C₅H₁₁ | 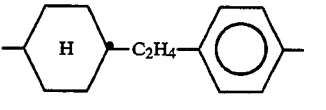 | F | F |
| n-C₃H₇ | 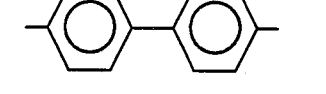 | H | H |
| n-C₃H₇ | 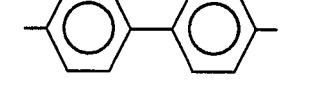 | H | F |
| n-C₃H₇ | 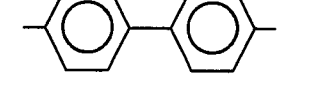 | F | F |
| n-C₅H₁₁ | 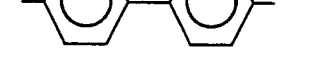 | H | H |
| n-C₅H₁₁ |  | H | F |

-continued
| R | $-(A^1-Z^1)_m-A^2-Z^2-$ | $L^1$ | $L^2$ |
|---|---|---|---|
| n-$C_5H_{11}$ | 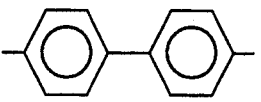 | F | F |
| n-$C_5H_{11}O$ | 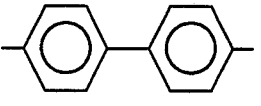 | H | F |
| $CH_3OCH_2$ | 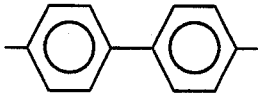 | F | F |
| n-$C_3H_7$ | 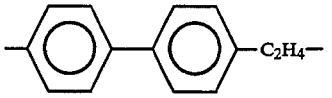 | H | H |
| n-$C_3H_7$ | 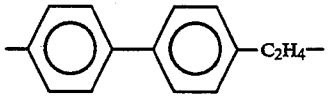 | H | F |
| n-$C_3H_7$ | 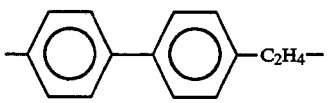 | F | F |
| n-$C_5H_{11}$ | 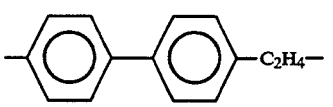 | H | H |
| n-$C_5H_{11}$ | 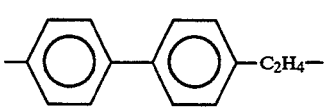 | H | F |
| n-$C_5H_{11}$ | 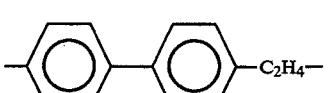 | F | F |
| n-$C_3H_7$ | 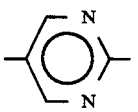 | H | H |
| n-$C_3H_7$ | 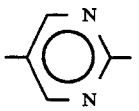 | H | F |
| n-$C_3H_7$ | 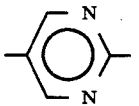 | F | F |
| n-$C_5H_{11}$ | 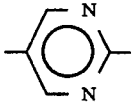 | H | H |

-continued

| R | $-(A^1-Z^1)_m-A^2-Z^2-$ | $L^1$ | $L^2$ |
|---|---|---|---|
| n-C$_5$H$_{11}$ | pyrazine (2,5-diN) | H | F |
| n-C$_5$H$_{11}$ | pyrazine (2,5-diN) | F | F |
| n-C$_5$H$_{11}$ | pyridine | H | H |
| n-C$_5$H$_{11}$ | pyridine | H | F |
| n-C$_5$H$_{11}$ | pyridine | F | F |
| n-C$_3$H$_7$ | pyridine | H | H |
| n-C$_3$H$_7$ | pyridine | H | F |
| n-C$_3$H$_7$ | pyridine | F | F |
| n-C$_3$H$_7$ | phenyl-(3,5-diF-phenyl) | H | H |
| n-C$_5$H$_{11}$ | phenyl-(3,5-diF-phenyl) | H | H |
| n-C$_3$H$_7$ | 1,3-dioxane | H | H |
| n-C$_3$H$_7$ | 1,3-dioxane | H | F |

-continued

| R | —(A¹—Z¹)ₘ—A²—Z²— | L¹ | L² |
|---|---|---|---|
| n-C₃H₇ | dioxane ring | F | F |
| n-C₅H₁₁ | dioxane ring | H | H |
| n-C₅H₁₁ | dioxane ring | H | F |
| n-C₅H₁₁ | dioxane ring | F | F |
| n-C₃H₇ | cyclohexyl–(3,5-diF-phenyl) | H | H |
| n-C₃H₇ | cyclohexyl–(3,5-diF-phenyl) | H | F |
| n-C₃H₇ | cyclohexyl–(3,5-diF-phenyl) | F | F |
| n-C₅H₁₁ | cyclohexyl–(3,5-diF-phenyl) | H | H |
| n-C₅H₁₁ | cyclohexyl–(3,5-diF-phenyl) | H | F |
| n-C₅H₁₁ | cyclohexyl–(3,5-diF-phenyl) | F | F |

EXAMPLE 10

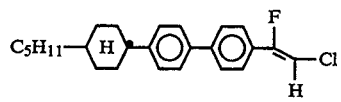

0.5 mol of n-pentylcyclohexylbiphenyl is treated, analogously to Example 9, first with 0.52 mol of chloroacetyl chloride, then with DAST and potassium tert.-butylate. C 44 N 93.8 I.

The following compounds of the formula

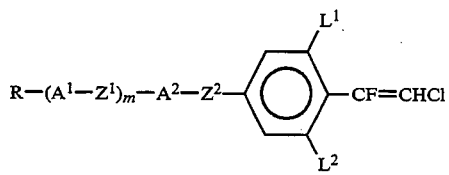

are prepared analogously.

| R | $-(A^1-Z^1)_m-A^2-Z^2-$ | $L^1$ | $L^2$ | |
|---|---|---|---|---|
| n-C$_3$H$_7$ | phenyl | H | H | |
| n-C$_3$H$_7$ | phenyl | H | F | |
| n-C$_3$H$_7$ | phenyl | F | F | |
| n-C$_5$H$_{11}$ | phenyl | H | H | C 148 I |
| n-C$_5$H$_{11}$ | phenyl | H | F | |
| n-C$_5$H$_{11}$ | phenyl | F | F | |
| CH$_3$CH$_2$O | phenyl | H | F | |
| CH$_2$=CHCH$_2$CH$_2$ | phenyl | F | F | |
| n-C$_3$H$_7$ | trans-cyclohexyl | H | H | |
| n-C$_3$H$_7$ | trans-cyclohexyl | H | F | |
| n-C$_3$H$_7$ | trans-cyclohexyl | F | F | |

-continued

| R | —(A¹—Z¹)ₘ—A²—Z²— | L¹ | L² | |
|---|---|---|---|---|
| n-C₅H₁₁ | (cyclohexane) | H | H | C 44 N 93.8 I |
| n-C₅H₁₁ | (cyclohexane) | H | F | |
| n-C₅H₁₁ | (cyclohexane) | F | F | C 36 N 31 I |
| n-C₂H₅ | (bicyclohexane) | H | H | |
| n-C₂H₅ | (bicyclohexane) | H | F | |
| n-C₂H₅ | (bicyclohexane) | F | F | |
| n-C₃H₇ | (bicyclohexane) | H | H | C 98 N 271.9 I |
| n-C₃H₇ | (bicyclohexane) | H | F | |
| n-C₃H₇ | (bicyclohexane) | F | F | C 89 N 219.3 I |
| n-C₅H₁₁ | (bicyclohexane) | H | H | |
| n-C₅H₁₁ | (bicyclohexane) | H | F | |
| n-C₅H₁₁ | (bicyclohexane) | F | F | |
| CH₂=CHCH₂CH₂ | (bicyclohexane) | H | H | |

| R | $-(A^1-Z^1)_m-A^2-Z^2-$ | $L^1$ | $L^2$ |
|---|---|---|---|
| n-C$_3$H$_7$ | 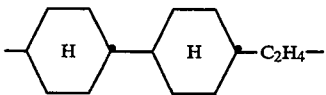 | H | H |
| n-C$_3$H$_7$ | 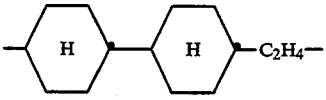 | H | F |
| n-C$_3$H$_7$ | 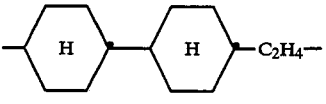 | F | F |
| n-C$_5$H$_{11}$ | 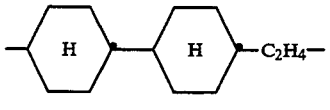 | H | H |
| n-C$_5$H$_{11}$ | 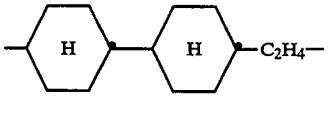 | H | F |
| n-C$_5$H$_{11}$ | 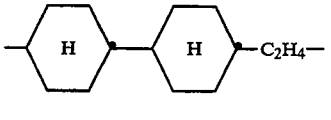 | F | F |
| n-C$_3$H$_7$ | 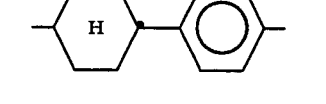 | H | F |
| n-C$_3$H$_7$ | 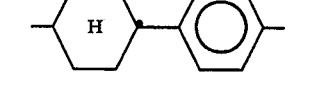 | F | F |
| n-C$_5$H$_{11}$ | 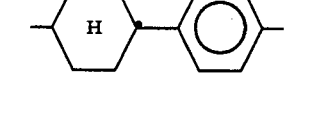 | H | F |
| n-C$_5$H$_{11}$ |  | F | F |
| n-C$_3$H$_7$ |  | H | H |
| n-C$_3$H$_7$ |  | H | F |
| n-C$_3$H$_7$ |  | F | F |

-continued

| R | $-(A^1-Z^1)_m-A^2-Z^2-$ | $L^1$ | $L^2$ |
|---|---|---|---|
| n-C$_5$H$_{11}$ | [cyclohexyl]-[phenyl]-C$_2$H$_4$- | H | H |
| n-C$_5$H$_{11}$ | [cyclohexyl]-[phenyl]-C$_2$H$_4$- | H | F |
| n-C$_5$H$_{11}$ | [cyclohexyl]-[phenyl]-C$_2$H$_4$- | F | F |
| n-C$_3$H$_7$ | [cyclohexyl]-C$_2$H$_4$-[phenyl]- | H | H |
| n-C$_3$H$_7$ | [cyclohexyl]-C$_2$H$_4$-[phenyl]- | H | F |
| n-C$_3$H$_7$ | [cyclohexyl]-C$_2$H$_4$-[phenyl]- | F | F |
| n-C$_5$H$_{11}$ | [cyclohexyl]-C$_2$H$_4$-[phenyl]- | H | H |
| n-C$_5$H$_{11}$ | [cyclohexyl]-C$_2$H$_4$-[phenyl]- | H | F |
| n-C$_5$H$_{11}$ | [cyclohexyl]-C$_2$H$_4$-[phenyl]- | F | F |
| n-C$_3$H$_7$ | [phenyl]-[phenyl]- | H | H |
| n-C$_3$H$_7$ | [phenyl]-[phenyl]- | H | F |
| n-C$_3$H$_7$ | [phenyl]-[phenyl]- | F | F |
| n-C$_5$H$_{11}$ | [phenyl]-[phenyl]- | H | H |

-continued
| R | —(A¹—Z¹)ₘ—A²—Z²— | L¹ | L² |
|---|---|---|---|
| n-C₅H₁₁ | 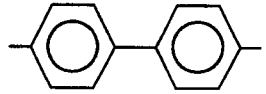 | H | F |
| n-C₅H₁₁ | 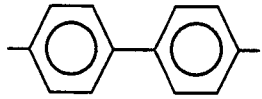 | F | F |
| n-C₅H₁₁O | 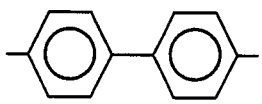 | H | F |
| CH₃OCH₂ | 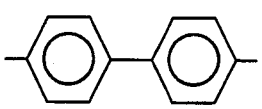 | F | F |
| n-C₃H₇ | 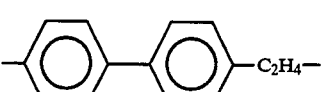 | H | H |
| n-C₃H₇ | 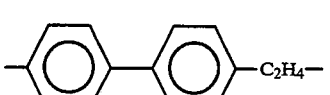 | H | F |
| n-C₃H₇ | 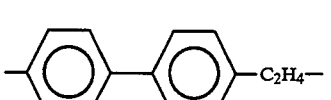 | F | F |
| n-C₅H₁₁ | 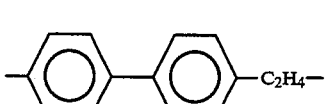 | H | H |
| n-C₅H₁₁ | 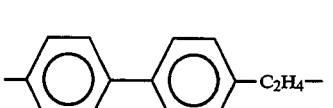 | H | F |
| n-C₅H₁₁ |  | F | F |
| n-C₃H₇ | 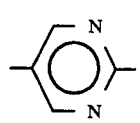 | H | H |
| n-C₃H₇ | 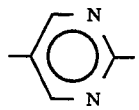 | H | F |
| n-C₃H₇ | 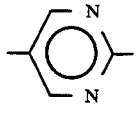 | F | F |

-continued

| R | $-(A^1-Z^1)_m-A^2-Z^2-$ | $L^1$ | $L^2$ |
|---|---|---|---|
| n-C$_5$H$_{11}$ | pyrimidine-2,5-diyl | H | H |
| n-C$_5$H$_{11}$ | pyrimidine-2,5-diyl | H | F |
| n-C$_5$H$_{11}$ | pyrimidine-2,5-diyl | F | F |
| n-C$_5$H$_{11}$ | pyridine-2,5-diyl | H | H |
| n-C$_5$H$_{11}$ | pyridine-2,5-diyl | H | F |
| n-C$_5$H$_{11}$ | pyridine-2,5-diyl | F | F |
| n-C$_3$H$_7$ | pyridine-2,5-diyl | H | H |
| n-C$_3$H$_7$ | pyridine-2,5-diyl | H | F |
| n-C$_3$H$_7$ | pyridine-2,5-diyl | F | F |
| n-C$_3$H$_7$ | 3,5-difluorobiphenyl-4,4'-diyl | H | H |
| n-C$_5$H$_{11}$ | 3,5-difluorobiphenyl-4,4'-diyl | H | H |
| n-C$_3$H$_7$ | 1,3-dioxane-2,5-diyl | H | H |

-continued
| R | $-(A^1-Z^1)_m-A^2-Z^2-$ | $L^1$ | $L^2$ |
|---|---|---|---|
| n-C$_3$H$_7$ | 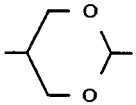 | H | F |
| n-C$_3$H$_7$ | 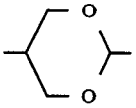 | F | F |
| n-C$_5$H$_{11}$ | 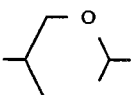 | H | H |
| n-C$_5$H$_{11}$ | 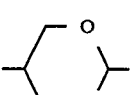 | H | F |
| n-C$_5$H$_{11}$ | 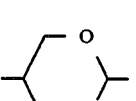 | F | F |
| n-C$_3$H$_7$ | 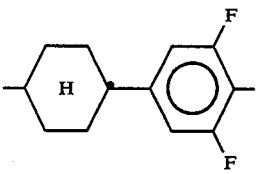 | H | H |
| n-C$_3$H$_7$ | 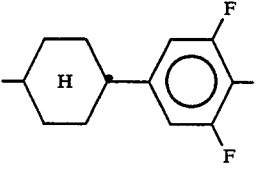 | H | F |
| n-C$_3$H$_7$ | 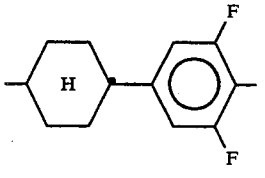 | F | F |
| n-C$_5$H$_{11}$ | 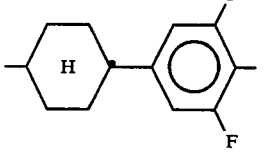 | H | H |
| n-C$_5$H$_{11}$ | 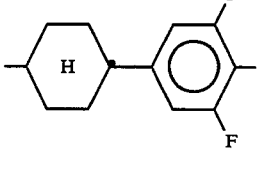 | H | F |

| R | $-(A^1-Z^1)_m-A^2-Z^2-$ | $L^1$ | $L^2$ |
|---|---|---|---|
| n-C$_5$H$_{11}$ | -continued 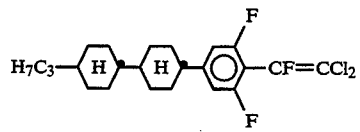 | F | F |

EXAMPLE 11

H$_7$C$_3$—(H)—(H)—⟨2,6-F$_2$-phenyl⟩—CF=CCl$_2$

A solution of 54 ml of BuLi in ether (89 mmol) is added at −78° C. to a mixture of 76 mmol of n-propyl-cyclohexylcyclohexyl-2,6-difluorobenzene and 100 ml of ether. The mixture is stirred for a further 0.5 hour and then cooled to −90° C., and 0.147 mol of dichlorodifluoroethylene is added to the reaction mixture. The mixture is stirred at −78° C. for a further 1 hour and then slowly warmed to −30° C. The mixture is subsequently subjected to customary work-up.

The following compounds of the formula $$R-(A^1-Z^1)_m-A^2-Z^2-\underset{L^2}{\overset{L^1}{\bigcirc}}-CF=CCl_2$$

are prepared analogously:

| R | $-(A^1-Z^1)_m-A^2-Z^2-$ | $L^1$ | $L^2$ |
|---|---|---|---|
| n-C$_3$H$_7$ | —(H)—(H)— | F | H |
| n-C$_5$H$_{11}$ | —(H)—(H)— | H | H |
| n-C$_5$H$_{11}$ | —(H)—(H)— | F | H |
| CH$_3$OCH$_2$ | —(H)—(H)— | F | H |
| CH$_3$CH$_2$O | —(H)—(H)— | F | F |
| CH$_2$=CHCH$_2$ | —(H)—(H)— | F | F |
| n-C$_3$H$_7$ | —⟨O⟩—⟨O⟩— | H | F |
| n-C$_3$H$_7$ | —⟨O⟩—⟨O⟩— | F | F |
| n-C$_5$H$_{11}$ | —⟨O⟩—⟨O⟩— | H | H |
| n-C$_5$H$_{11}$ | —⟨O⟩—⟨O⟩— | F | F |
| CH$_3$CH$_2$O | —⟨O⟩—⟨O⟩— | F | F |
| CH$_3$OCH$_2$ | —⟨O⟩—⟨O⟩— | F | F |
| CH$_2$=CHCH$_2$ | —⟨O⟩—⟨O⟩— | F | H |
| n-C$_3$H$_7$ | —⟨O⟩—CH$_2$CH$_2$—⟨O⟩— | H | F |
| n-C$_3$H$_7$ | —⟨O⟩—CH$_2$CH$_2$—⟨O⟩— | F | H |
| n-C$_5$H$_{11}$ | —⟨O⟩—CH$_2$CH$_2$—⟨O⟩— | H | H |
| n-C$_5$H$_{11}$ | —⟨O⟩—CH$_2$CH$_2$—⟨O⟩— | F | H |
| CH$_3$CH$_2$O | —⟨O⟩—CH$_2$CH$_2$—⟨O⟩— | F | H |
| CH$_3$OCH$_2$ | —⟨O⟩—CH$_2$CH$_2$—⟨O⟩— | F | H |
| CH$_2$=CHCH$_2$ | —⟨O⟩—CH$_2$CH$_2$—⟨O⟩— | F | F |
| n-C$_3$H$_7$ | —(H)—⟨O⟩— | H | F |
| n-C$_3$H$_7$ | —(H)—⟨O⟩— | F | F |
| n-C$_5$H$_{11}$ | —(H)—⟨O⟩— | H | F |
| n-C$_5$H$_{11}$ | —(H)—⟨O⟩— | F | F |

-continued

| R | $-(A^1-Z^1)_m-A^2-Z^2-$ | $L^1$ | $L^2$ |
|---|---|---|---|
| n-C$_6$H$_{13}$ | -[H]-[O]- | H | H |
| n-C$_6$H$_{13}$ | -[H]-[O]- | F | F |
| CH$_3$CH$_2$O | -[H]-[O]- | F | F |
| CH$_3$OCH$_2$ | -[H]-[O]- | F | H |
| CH$_2$=CHCH$_2$CH$_2$ | -[H]-[O]- | F | F |
| n-C$_3$H$_7$ | -[H]-[O(F,F)]- | F | F |
| n-C$_5$H$_{11}$ | -[H]-[O(F,F,F)]- | F | F |

EXAMPLE 12

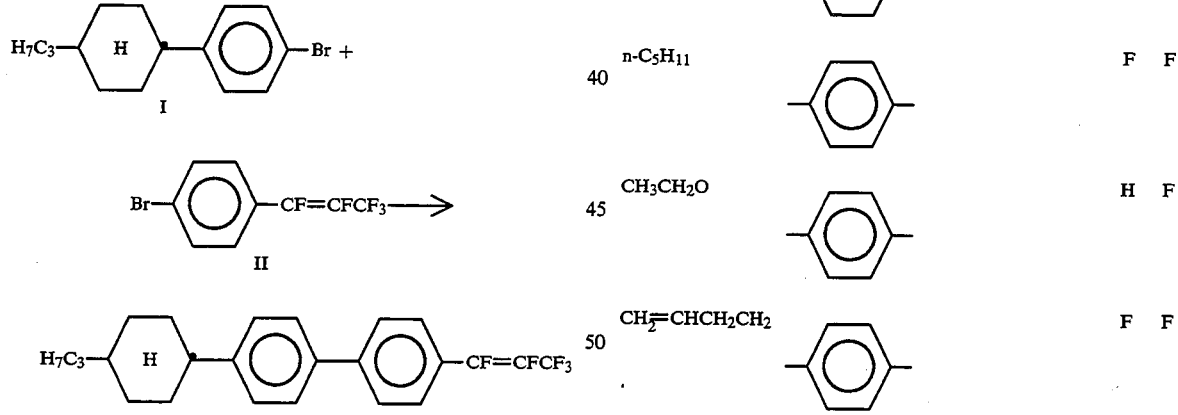

0.48 mol of butyllithium (15% in hexane) is added dropwise over the course of 45 minutes at −75° C. to 0.48 mol of 4-(4-trans-propylcyclohexyl)-1-bromobenzene in 800 ml of THF. The mixture is subsequently first stirred for 0.5 hour, then a cooled solution of 0.24 mol of zinc bromide in 200 ml of THF is added dropwise, and the mixture is stirred for a further 0.5 hour at −75° C. 0.4 mol of II and 7 g of PdCl$_2$ dppf are added at −75° C., and the mixture is stirred at room temperature for a further 72 hours. 500 ml of saturated ammonium chloride solution are added, and the organic phase is separated off and subjected to customary work-up.

The following compounds of the formula I

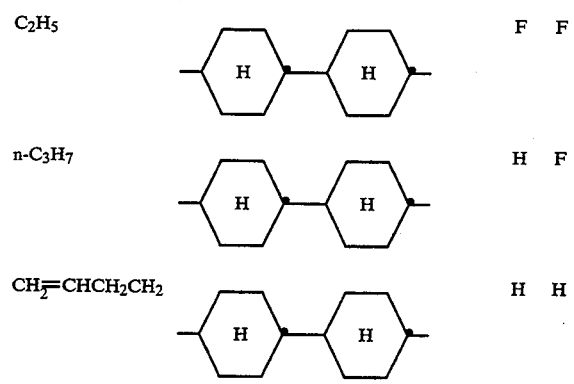

are prepared analogously:

| R | $-(A^1-Z^1)_m-A^2-Z^2-$ | $L^1$ | $L^2$ |
|---|---|---|---|
| n-C$_3$H$_7$ | -[O]- | H | H |
| n-C$_3$H$_7$ | -[O]- | H | F |
| n-C$_3$H$_7$ | -[O]- | F | F |
| n-C$_5$H$_{11}$ | -[O]- | H | H |
| n-C$_5$H$_{11}$ | -[O]- | H | F |
| n-C$_5$H$_{11}$ | -[O]- | F | F |
| CH$_3$CH$_2$O | -[O]- | H | F |
| CH$_2$=CHCH$_2$CH$_2$ | -[O]- | F | F |
| C$_2$H$_5$ | -[H]-[H]- | F | F |
| n-C$_3$H$_7$ | -[H]-[H]- | H | F |
| CH$_2$=CHCH$_2$CH$_2$ | -[H]-[H]- | H | H |

| R | —(A¹—Z¹)ₘ—A²—Z²— | L¹ | L² |
|---|---|---|---|
| n-C₃H₇ | 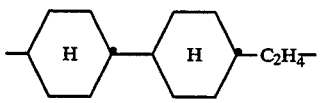 | H | H |
| n-C₅H₁₁ | 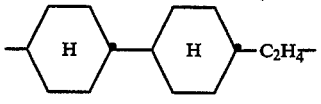 | H | F |
| CH₃CH₂OCH₂ | 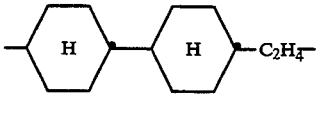 | F | F |
| n-C₃H₇ | 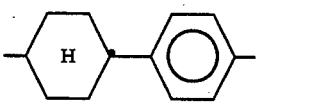 | H | F |
| n-C₃H₇ | 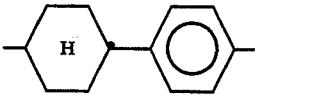 | F | F |
| n-C₅H₁₁ | 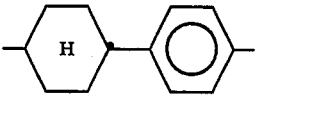 | H | H |
| n-C₅H₁₁ | 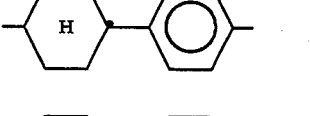 | F | H |
| n-C₃H₇ |  | H | H |
| n-C₅H₁₁ | 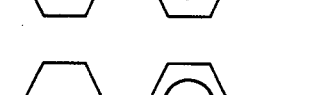 | H | F |
| n-C₅H₁₁ | 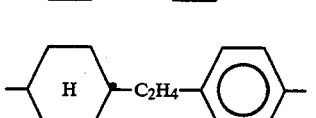 | F | F |
| n-C₃H₇ | 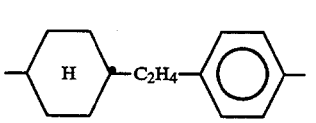 | H | H |
| n-C₃H₇ | 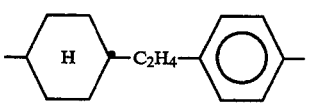 | H | F |
| n-C₅H₁₁ |  | F | F |
| R | —(A¹—Z¹)ₘ—A²—Z²— | L¹ | L² |
|---|---|---|---|
| n-C₅H₁₁ | 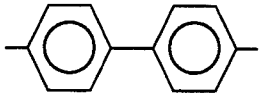 | H | H |
| n-C₅H₁₁O | 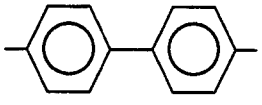 | H | F |
| CH₃OCH₂ | 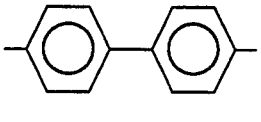 | F | F |
| n-C₃H₇ | 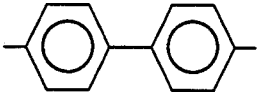 | H | H |
| n-C₄H₉ | 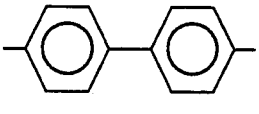 | H | F |
| n-C₅H₁₁ | 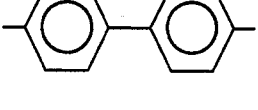 | F | F |
| n-C₃H₇ |  | H | F |
| n-C₅H₁₁ |  | H | F |
| n-C₅H₁₁ | 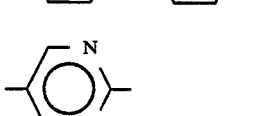 | F | F |
| n-C₃H₇ | 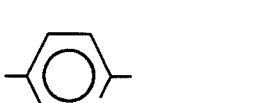 | H | H |
| n-C₅H₁₁ |  | F | F |
EXAMPLE 13
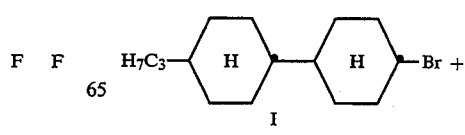

-continued

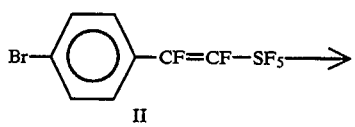

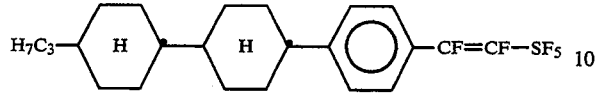

0.56 mol of zinc bromide and then 2.24 mol of lithium are added at 0° C. to 1.12 mol of I in 1500 ml of THF: toluene=1:4. The mixture is subsequently treated with ultrasound for 4 hours at 0°-10° C. with stirring. 0.56 mol of II and 12.3 g of PdCl$_2$-dppf are added, the cooling is removed, and the mixture is stirred at room temperature for a further 72 hours. The mixture is poured into 1000 ml of ammonium chloride solution and stirred for 15 minutes. The organic phase is separated off and subjected to customary work-up.

The following compounds of the formula

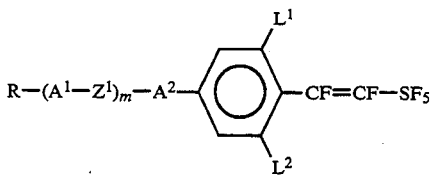

are prepared analogously:

| R | $-(A^1-Z^1)_m-A^2-Z^2-$ | $L^1$ | $L^2$ |
|---|---|---|---|
| n-C$_3$H$_7$ | ⬡— | H | H |
| n-C$_3$H$_7$ | ⬡— | H | F |
| n-C$_3$H$_7$ | ⬡— | F | F |
| n-C$_5$H$_{11}$ | ⬡— | H | H |
| n-C$_5$H$_{11}$ | ⬡— | H | F |
| n-C$_5$H$_{11}$ | ⬡— | F | F |
| CH$_3$CH$_2$O | ⬡— | H | F |
| CH$_2$=CHCH$_2$CH$_2$ | ⬡— | F | F |
| n-C$_3$H$_7$ | ⬢H— | H | H |
| n-C$_5$H$_{11}$ | ⬢H— | H | F |

| R | $-(A^1-Z^1)_m-A^2-Z^2-$ | $L^1$ | $L^2$ |
|---|---|---|---|
| n-C$_6$H$_{13}$OCH$_2$ |  | F | F |
| n-C$_2$H$_5$ | 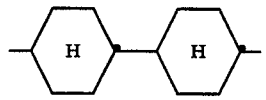 | F | F |
| n-C$_3$H$_7$ | 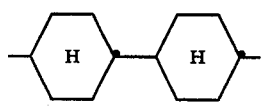 | H | F |
| CH$_2$=CHCH$_2$CH$_2$ | 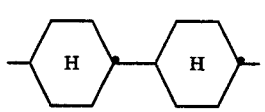 | H | H |
| n-C$_3$H$_7$ | 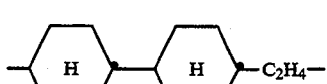 | H | H |
| n-C$_5$H$_{11}$ | 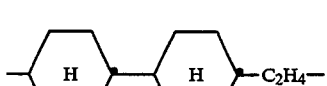 | H | F |
| CH$_3$CH$_2$OCH$_2$ | 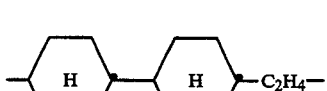 | F | F |
| n-C$_3$H$_7$ |  | H | H |
| n-C$_5$H$_{11}$ |  | H | H |
| n-C$_3$H$_7$ |  | F | F |
| n-C$_3$H$_7$ | 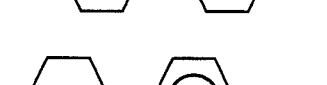 | H | H |
| n-C$_5$H$_{11}$ | 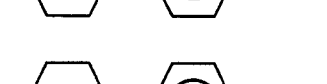 | H | F |
| n-C$_5$H$_{11}$OCH$_2$ | 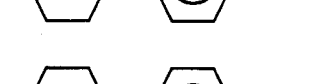 | F | F |

-continued

| R | —(A¹—Z¹)ₘ—A²—Z²— | L¹ | L² |
|---|---|---|---|
| n-C₃H₇ | cyclohexyl–C₂H₄–phenyl | H | H |
| n-C₃H₇ | cyclohexyl–C₂H₄–phenyl | H | F |
| n-C₅H₁₁ | cyclohexyl–C₂H₄–phenyl | F | F |
| n-C₅H₁₁ | phenyl–phenyl | H | H |
| n-C₅H₁₁O | phenyl–phenyl | H | F |
| CH₃OCH₂ | phenyl–phenyl | F | F |
| n-C₃H₇ | phenyl–phenyl–C₂H₄– | H | H |
| n-C₄H₉ | phenyl–phenyl–C₂H₄– | H | F |
| n-C₅H₁₁ | phenyl–phenyl–C₂H₄– | F | F |
| n-C₃H₇ | phenyl–phenyl–C₂H₄– | H | F |
| n-C₅H₁₁ | phenyl–phenyl–C₂H₄– | H | F |
| n-C₅H₁₁ | phenyl–phenyl–C₂H₄– | F | F |
| n-C₃H₇ | pyrimidinyl | H | H |

| R | —(A¹—Z¹)$_m$—A²—Z²— | L¹ | L² |
|---|---|---|---|
| n-C$_5$H$_{11}$ | (pyridine/pyrazine ring) | F | F |

EXAMPLE 14

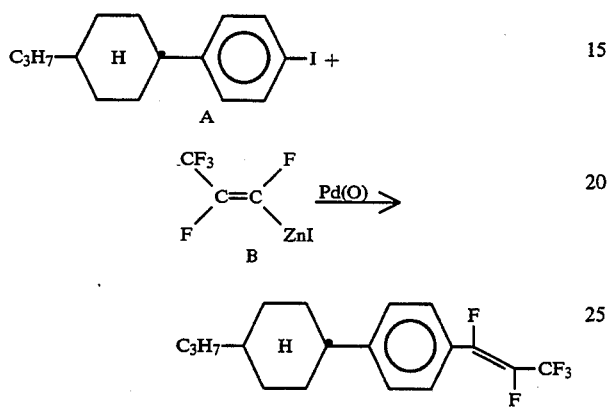

60 mmol of (Z)-CF$_3$CF=CF—I are reacted with 5.0 g of activated zinc in triethylene glycol dimethyl ether (triglyme) by the method described by Burton et al. to give the corresponding zinc derivative B (Dolliest et al., J. Am. Chem. Soc. 109, 219–225, 1987). 0.05 of 1-(4-propyl-trans-cyclohexyl)-4-iodobenzene A and 1.4 g of Pd(PPh$_3$)$_4$ are added to the solution of the zinc derivative, and the mixture is warmed at 40° C. for 48 hours. The mixture is then poured into water and subjected to customary work-up.

The following compounds of the formula

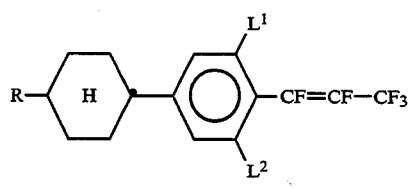

are prepared analogously:

| R | —(A¹—Z¹)$_m$—A²—Z²— | L¹ | L² |
|---|---|---|---|
| C$_2$H$_5$ | —⟨H⟩— | H | H |
| C$_2$H$_5$ | —⟨H⟩— | H | F |
| C$_2$H$_5$ | —⟨H⟩— | F | F |
| n-C$_3$H$_7$ | —⟨H⟩— | H | F |
| n-C$_3$H$_7$ | —⟨H⟩— | F | F |
| n-C$_5$H$_{11}$ | —⟨H⟩— | H | H |
| n-C$_5$H$_{11}$ | —⟨H⟩— | H | F |
| n-C$_5$H$_{11}$ | —⟨H⟩— | F | F |
| CH$_3$CH$_2$O | —⟨H⟩— | H | F |
| CH$_2$=CHCH$_2$H$_2$ | —⟨H⟩— | H | F |

EXAMPLE 15

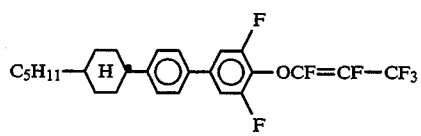

19.07 mmol of 2,6-difluoro-4-[4-(4-pentylcyclohexyl)-phenyl]phenyl 1,1,1,2,3,4-hexafluoropropyl ether are dissolved in 100 ml of THF. A solution of 20 mmol of lithium tetramethylpiperidine (prepared at −20° C. from mmol of 2,2,6,6-tetramethylpiperidine in 10 ml of THF and 12.5 ml of a 1.6 molar solution of butyllithium in hexane) is added dropwise thereto with cooling (−78° C.). The mixture is allowed to warm slowly to room temperature. The mixture is subsequently refluxed for 0.5 hour. The solution is then evaporated to dryness at room temperature under reduced pressure. The residue is extracted with dichloromethane and subjected to customary work-up.

The following compounds of the formula
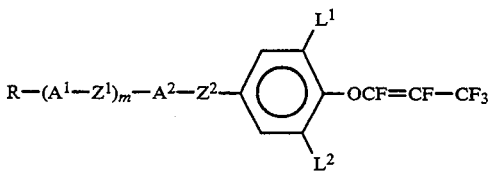
are prepared analogously:
| R | $-(A^1-Z^1)_m-A^2-Z^2-$ | $L^1$ | $L^2$ |
|---|---|---|---|
| n-$C_3H_7$ | –⌬– | H | H |
| n-$C_3H_7$ | –⌬– | H | F |
| n-$C_3H_7$ | –⌬– | F | F |
| n-$C_5H_{11}$ | –⌬– | H | H |
| n-$C_5H_{11}$ | –⌬– | H | F |
| n-$C_5H_{11}$ | –⌬– | F | F |
| $CH_3CH_2O$ | –⌬– | H | F |
| $CH_2=CHCH_2CH_2$ | –⌬– | F | F |
| n-$C_3H_7$ | –⟨H⟩– | H | F |
| n-$C_5H_{11}$ | –⟨H⟩– | H | F |
| $C_2H_5$ | –⟨H⟩–⟨H⟩– | F | F |

-continued
| R | $-(A^1-Z^1)_m-A^2-Z^2-$ | $L^1$ | $L^2$ |
|---|---|---|---|
| n-C₃H₇ | 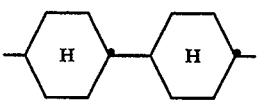 | H | F |
| CH₂=CHCH₂CH₂ | 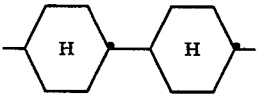 | H | H |
| n-C₃H₇ | 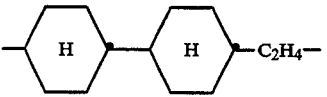 | H | H |
| n-C₅H₁₁ | 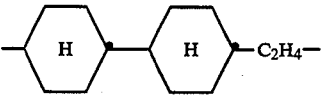 | H | F |
| CH₃CH₂OCH₂ | 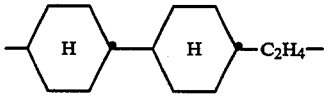 | F | F |
| n-C₃H₇ | 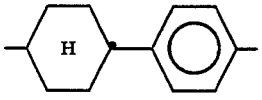 | H | F |
| n-C₃H₇ | 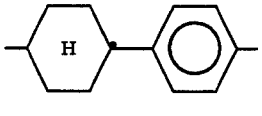 | F | F |
| n-C₅H₁₁ | 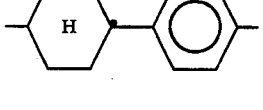 | H | H |
| n-C₅H₁₁ |  | F | H |
| n-C₅H₁₁ |  | F | H |
| n-C₃H₇ |  | H | H |
| n-C₅H₁₁ |  | H | F |
| n-C₅H₁₁ |  | F | F |

-continued

| R | $-(A^1-Z^1)_m-A^2-Z^2-$ | $L^1$ | $L^2$ |
|---|---|---|---|
| n-C$_3$H$_7$ | —[Cy]—C$_2$H$_4$—[Ph]— | H | H |
| n-C$_3$H$_7$ | —[Cy]—C$_2$H$_4$—[Ph]— | H | F |
| n-C$_5$H$_{11}$ | —[Cy]—C$_2$H$_4$—[Ph]— | F | F |
| n-C$_5$H$_{11}$ | —[Ph]—[Ph]— | H | H |
| n-C$_5$H$_{11}$O | —[Ph]—[Ph]— | H | F |
| CH$_3$OCH$_2$ | —[Ph]—[Ph]— | F | F |
| n-C$_3$H$_7$ | —[Ph]—[Ph]—C$_2$H$_4$— | H | H |
| n-C$_4$H$_9$ | —[Ph]—[Ph]—C$_2$H$_4$— | H | F |
| n-C$_5$H$_{11}$ | —[Ph]—[Ph]—C$_2$H$_4$— | F | F |
| n-C$_3$H$_7$ | —[Ph]—[Ph]—C$_2$H$_4$— | H | F |
| n-C$_5$H$_{11}$ | —[Ph]—[Ph]—C$_2$H$_4$— | H | F |
| n-C$_5$H$_{11}$ | —[Ph]—[Ph]—C$_2$H$_4$— | F | F |
| n-C$_3$H$_7$ | —[Pyrimidine]— | H | H |

-continued

| R | $-(A^1-Z^1)_m-A^2-Z^2-$ | $L^1$ | $L^2$ |
|---|---|---|---|
| n-C$_5$H$_{11}$ | 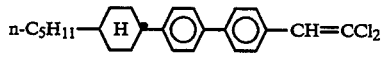 | F | F |

EXAMPLE 16 n-C$_5$H$_{11}$—(H)—(O)—(O)—CH=CCl$_2$ 3 eq. of triphenylphosphine are dissolved in absolute THF (5.0 ml/g of PPh$_3$), and 1.5 eq. of CCl$_4$ are added at room temperature. The resultant mixture is stirred for 2 hours, and 1.5 eq. of activated magnesium are subsequently added. The mixture is then stirred for a further 0.5 hour. 1.0 eq of n-pentylcyclohexylphenyl-4-benzaldehyde is added, and the mixture is stirred for hours and filtered through silica gel. The filtrate is subjected to customary work-up.

The following compounds of the formula

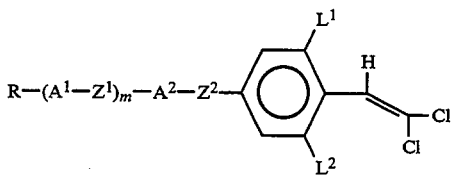

are prepared analogously:

| R | $-(A^1-Z^1)_m-A^2-Z^2-$ | $L^1$ | $L^2$ |
|---|---|---|---|
| n-C$_3$H$_7$ | (O)- | H | H |
| n-C$_3$H$_7$ | (O)- | H | F |
| n-C$_3$H$_7$ | (O)- | F | F |
| n-C$_5$H$_{11}$ | (O)- | H | H |
| n-C$_5$H$_{11}$ | (O)- | H | F |
| n-C$_5$H$_{11}$ | (O)- | F | F |
| CH$_3$CH$_2$O | (O)- | H | F |
| CH$_2$=CHCH$_2$CH$_2$ | (O)- | F | F |
| n-C$_3$H$_7$ | (H)- | H | H |

-continued

| R | $-(A^1-Z^1)_m-A^2-Z^2-$ | $L^1$ | $L^2$ |
|---|---|---|---|
| n-C$_3$H$_7$ | Cy | H | F |
| n-C$_3$H$_7$ | Cy | F | F |
| n-C$_5$H$_{11}$ | Cy | H | H |
| n-C$_5$H$_{11}$ | Cy | H | F |
| n-C$_5$H$_{11}$ | Cy | F | F |
| n-C$_2$H$_5$ | Cy-Cy | H | H |
| n-C$_2$H$_5$ | Cy-Cy | H | F |
| n-C$_2$H$_5$ | Cy-Cy | F | F |
| n-C$_3$H$_7$ | Cy-Cy | H | H |
| n-C$_3$H$_7$ | Cy-Cy | H | F |
| n-C$_3$H$_7$ | Cy-Cy | F | F |
| n-C$_5$H$_{11}$ | Cy-Cy | H | H |
| n-C$_5$H$_{11}$ | Cy-Cy | H | F |

|   |   |   |   |
|---|---|---|---|
| R | $-(A^1-Z^1)_m-A^2-Z^2-$ | $L^1$ | $L^2$ |
| n-C$_5$H$_{11}$ | H–H– | F | F |
| CH$_2$=CHCH$_2$CH$_2$ | H–H– | H | H |
| n-C$_3$H$_7$ | H–H–C$_2$H$_4$– | H | H |
| n-C$_3$H$_7$ | H–H–C$_2$H$_4$– | H | F |
| n-C$_3$H$_7$ | H–H–C$_2$H$_4$– | F | F |
| n-C$_5$H$_{11}$ | H–H–C$_2$H$_4$– | H | H |
| n-C$_5$H$_{11}$ | H–H–C$_2$H$_4$– | H | F |
| n-C$_5$H$_{11}$ | H–H–C$_2$H$_4$– | F | F |
| n-C$_3$H$_7$ | H–⌬– | H | H |
| n-C$_3$H$_7$ | H–⌬– | H | F |
| n-C$_3$H$_7$ | H–⌬– | F | F |
| n-C$_5$H$_{11}$ | H–⌬– | H | F |
| n-C$_5$H$_{11}$ | H–⌬– | F | F |

-continued

| R | —(A¹—Z¹)ₘ—A²—Z²— | L¹ | L² |
|---|---|---|---|
| n-C₃H₇ | —[H]—[Ph]—C₂H₄— | H | H |
| n-C₃H₇ | —[H]—[Ph]—C₂H₄— | H | F |
| n-C₃H₇ | —[H]—[Ph]—C₂H₄— | F | F |
| n-C₅H₁₁ | —[H]—[Ph]—C₂H₄— | H | H |
| n-C₅H₁₁ | —[H]—[Ph]—C₂H₄— | H | F |
| n-C₅H₁₁ | —[H]—[Ph]—C₂H₄— | F | F |
| n-C₃H₇ | —[H]—C₂H₄—[Ph]— | H | H |
| n-C₃H₇ | —[H]—C₂H₄—[Ph]— | H | F |
| n-C₃H₇ | —[H]—C₂H₄—[Ph]— | F | F |
| n-C₅H₁₁ | —[H]—C₂H₄—[Ph]— | H | H |
| n-C₅H₁₁ | —[H]—C₂H₄—[Ph]— | H | F |
| n-C₅H₁₁ | —[H]—C₂H₄—[Ph]— | F | F |
| n-C₃H₇ | —[Ph]—[Ph]— | H | H |

-continued
| R | −(A¹−Z¹)ₘ−A²−Z²− | L¹ | L² |
|---|---|---|---|
| n-C₃H₇ | 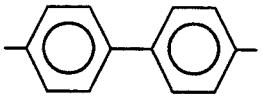 | H | F |
| n-C₃H₇ | 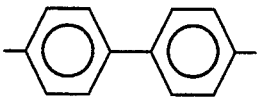 | F | F |
| n-C₅H₁₁ | 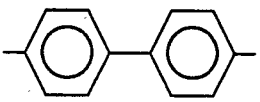 | H | H |
| n-C₅H₁₁ | 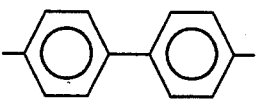 | H | F |
| n-C₅H₁₁ | 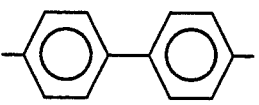 | F | F |
| n-C₅H₁₁O | 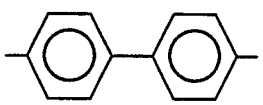 | H | F |
| CH₃OCH₂ | 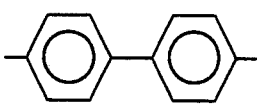 | F | F |
| n-C₃H₇ | 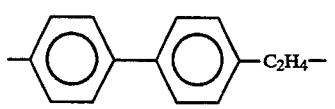 | H | H |
| n-C₃H₇ | 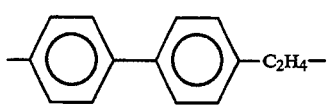 | H | F |
| n-C₃H₇ | 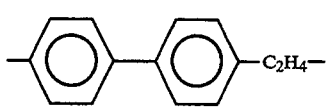 | F | F |
| n-C₅H₁₁ | 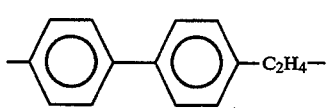 | H | H |
| n-C₅H₁₁ | 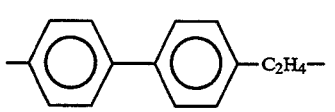 | H | F |
| n-C₅H₁₁ | 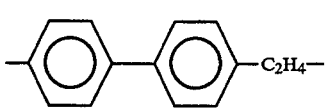 | F | F |

-continued
| R | −(A¹−Z¹)ₘ−A²−Z²− | L¹ | L² |
|---|---|---|---|
| n-C₃H₇ | 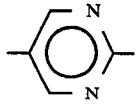 | H | H |
| n-C₃H₇ | 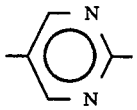 | H | F |
| n-C₃H₇ | 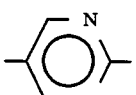 | F | F |
| n-C₅H₁₁ | 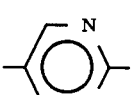 | H | H |
| n-C₅H₁₁ | 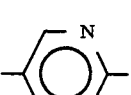 | H | F |
| n-C₅H₁₁ | 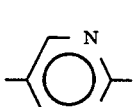 | F | F |
| n-C₅H₁₁ | 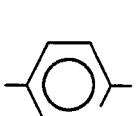 | H | H |
| n-C₅H₁₁ | 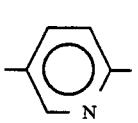 | H | F |
| n-C₅H₁₁ | 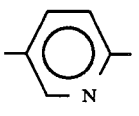 | F | F |
| n-C₃H₇ | 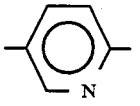 | H | H |
| n-C₃H₇ | 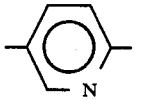 | H | F |
| n-C₃H₇ | 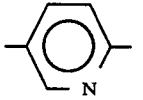 | F | F |

-continued

| R | $-(A^1-Z^1)_m-A^2-Z^2-$ | $L^1$ | $L^2$ |
|---|---|---|---|
| n-C$_3$H$_7$ | biphenyl with F at 3,5-positions | H | H |
| n-C$_5$H$_{11}$ | biphenyl with F at 3,5-positions | H | H |
| n-C$_3$H$_7$ | 1,3-dioxane | H | H |
| n-C$_3$H$_7$ | 1,3-dioxane | H | F |
| n-C$_3$H$_7$ | 1,3-dioxane | F | F |
| n-C$_5$H$_{11}$ | 1,3-dioxane | H | H |
| n-C$_5$H$_{11}$ | 1,3-dioxane | H | F |
| n-C$_5$H$_{11}$ | 1,3-dioxane | F | F |
| n-C$_3$H$_7$ | cyclohexyl-phenyl (3,5-diF) | H | H |
| n-C$_3$H$_7$ | cyclohexyl-phenyl (3,5-diF) | H | F |
| n-C$_3$H$_7$ | cyclohexyl-phenyl (3,5-diF) | F | F |

-continued

| R | $-(A^1-Z^1)_m-A^2-Z^2-$ | $L^1$ | $L^2$ |
|---|---|---|---|
| n-C$_5$H$_{11}$ | cyclohexyl-(2,5-difluoro)phenyl | H | H |
| n-C$_5$H$_{11}$ | cyclohexyl-(2,4-difluoro)phenyl | H | F |
| n-C$_5$H$_{11}$ | cyclohexyl-(2,3,5-trifluoro)phenyl | F | F |

EXAMPLE 17

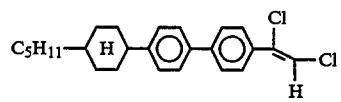

0.52 mol of chloroacetic acid is added dropwise at 0° C. with stirring to 0.6 mol of powdered aluminum chloride and 200 ml of dichloromethane. 0.5 mol of n-pentylcyclohexylbiphenyl is subsequently added to the mixture. The mixture is then stirred for a further hour and left to stand overnight. It is poured onto ice and subjected to customary work-up. The resultant chlorinated ketone is treated first with PCl$_5$ and then with KOH. The mixture is finally subjected to customary work-up.

The following compounds of the formula

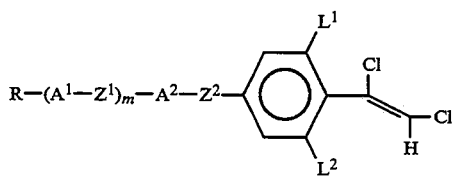

are prepared analogously:

| R | $-(A^1-Z^1)_m-A^2-Z^2-$ | $L^1$ | $L^2$ |
|---|---|---|---|
| n-C$_3$H$_7$ | phenyl | H | H |
| n-C$_3$H$_7$ | phenyl | H | F |
| n-C$_3$H$_7$ | phenyl | F | F |
| n-C$_5$H$_{11}$ | phenyl | H | H |
| n-C$_5$H$_{11}$ | phenyl | H | F |
| n-C$_5$H$_{11}$ | phenyl | F | F |
| CH$_3$CH$_2$O | phenyl | H | F |
| CH$_2$=CHCH$_2$CH$_2$ | phenyl | F | F |
| n-C$_3$H$_7$ | cyclohexyl | H | H |
| n-C$_3$H$_7$ | cyclohexyl | H | F |

-continued

| R | $-(A^1-Z^1)_m-A^2-Z^2-$ | $L^1$ | $L^2$ |
|---|---|---|---|
| n-C$_3$H$_7$ | 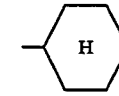 | F | F |
| n-C$_5$H$_{11}$ | 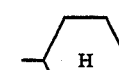 | H | H |
| n-C$_5$H$_{11}$ | 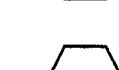 | H | F |
| n-C$_5$H$_{11}$ | 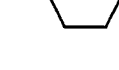 | F | F |
| n-C$_2$H$_5$ | 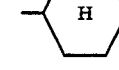 | H | H |
| n-C$_2$H$_5$ | 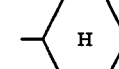 | H | F |
| n-C$_2$H$_5$ |  | F | F |
| n-C$_3$H$_7$ | 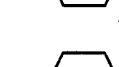 | H | H |
| n-C$_3$H$_7$ | 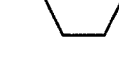 | H | F |
| n-C$_3$H$_7$ | 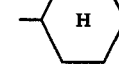 | F | F |
| n-C$_5$H$_{11}$ | 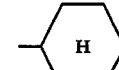 | H | H |
| n-C$_5$H$_{11}$ | 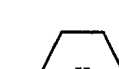 | H | F |
| n-C$_5$H$_{11}$ | 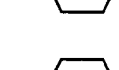 | F | F |

-continued

| R | $-(A^1-Z^1)_m-A^2-Z^2-$ | $L^1$ | $L^2$ |
|---|---|---|---|
| CH$_2$=CHCH$_2$CH$_2$ | 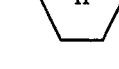 | H | H |
| n-C$_3$H$_7$ | 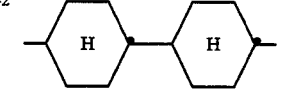 | H | H |
| n-C$_3$H$_7$ |  | H | F |
| n-C$_3$H$_7$ | 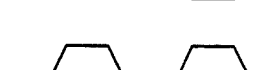 | F | F |
| n-C$_5$H$_{11}$ | 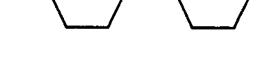 | H | H |
| n-C$_5$H$_{11}$ | 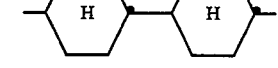 | H | F |
| n-C$_5$H$_{11}$ | 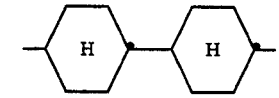 | F | F |
| n-C$_3$H$_7$ |  | H | F |
| n-C$_3$H$_7$ | 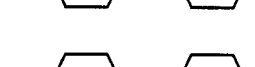 | F | F |
| n-C$_5$H$_{11}$ |  | H | F |
| n-C$_5$H$_{11}$ | 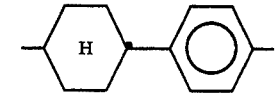 | F | F |
| n-C$_3$H$_7$ | 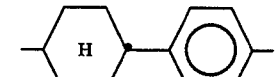 | H | H |
| n-C$_3$H$_7$ | 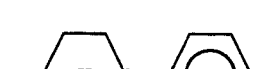 | H | F |

| R | —(A¹—Z¹)ₘ—A²—Z²— | L¹ | L² | R | —(A¹—Z¹)ₘ—A²—Z²— | L¹ | L² |
|---|---|---|---|---|---|---|---|
| n-C₃H₇ | 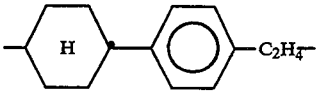 | F | F | n-C₅H₁₁ | 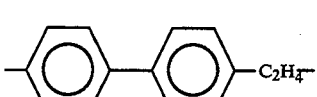 | H | H |
| n-C₅H₁₁ | 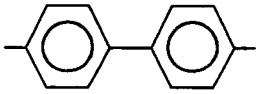 | H | H | n-C₅H₁₁ | 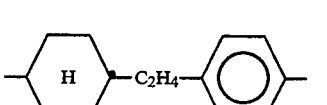 | H | F |
| n-C₅H₁₁ | 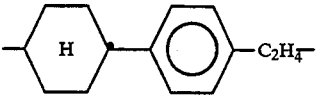 | H | F | n-C₅H₁₁ | 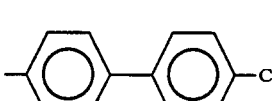 | F | F |
| n-C₅H₁₁ | 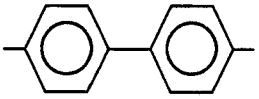 | F | F | n-C₅H₁₁O |  | H | F |
| n-C₃H₇ | 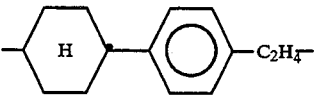 | H | H | CH₃OCH₂ | 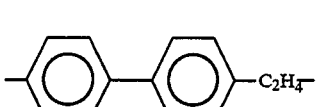 | F | F |
| n-C₃H₇ | 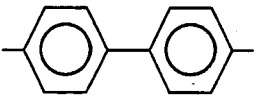 | H | F | n-C₃H₇ |  | H | H |
| n-C₃H₇ | 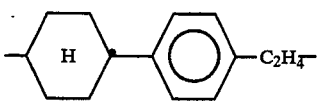 | F | F | n-C₃H₇ |  | H | F |
| n-C₅H₁₁ | 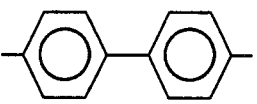 | H | H | n-C₃H₇ |  | F | F |
| n-C₅H₁₁ | 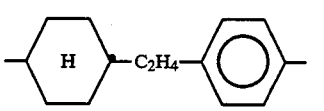 | H | F | n-C₅H₁₁ | 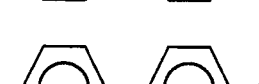 | H | H |
| n-C₅H₁₁ | 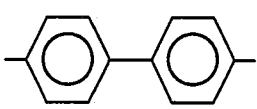 | F | F | n-C₅H₁₁ | 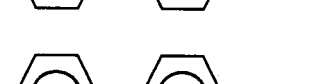 | H | F |
| n-C₃H₇ | 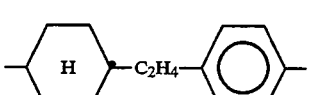 | H | H | n-C₅H₁₁ |  | F | F |
| n-C₃H₇ | 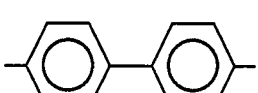 | H | F | n-C₃H₇ | 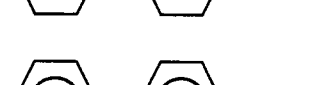 | H | H |
| n-C₃H₇ | 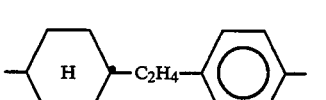 | F | F | n-C₃H₇ | 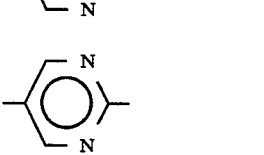 | H | F |

-continued
| R | —(A¹—Z¹)ₘ—A²—Z²— | L¹ | L² |
|---|---|---|---|
| n-C₃H₇ | 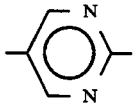 | F | F |
| n-C₅H₁₁ | 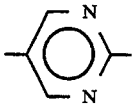 | H | H |
| n-C₅H₁₁ | 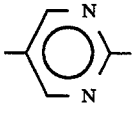 | H | F |
| n-C₅H₁₁ | 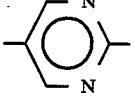 | F | F |
| n-C₅H₁₁ | 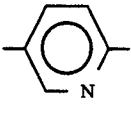 | H | H |
| n-C₅H₁₁ | 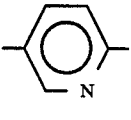 | H | F |
| n-C₅H₁₁ | 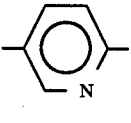 | F | F |
| n-C₃H₇ | 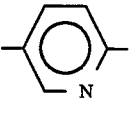 | H | H |
| n-C₃H₇ | 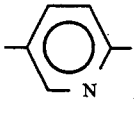 | H | F |
| n-C₃H₇ | 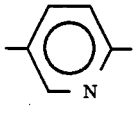 | F | F |
| n-C₃H₇ | 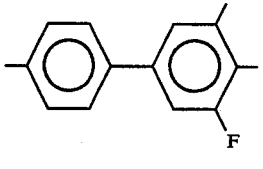 | H | H |
| n-C₅H₁₁ | 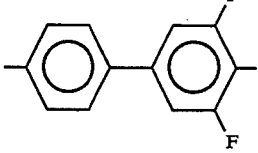 | H | H |
-continued
| R | —(A¹—Z¹)ₘ—A²—Z²— | L¹ | L² |
|---|---|---|---|
| n-C₃H₇ | 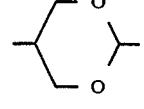 | H | H |
| n-C₃H₇ | 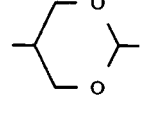 | H | F |
| n-C₃H₇ | 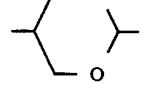 | F | F |
| n-C₅H₁₁ | 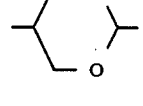 | H | H |
| n-C₅H₁₁ | 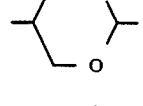 | H | F |
| n-C₅H₁₁ | 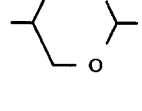 | F | F |
| n-C₃H₇ | 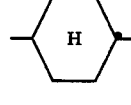 | H | H |
| n-C₃H₇ | 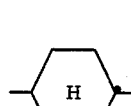 | H | F |
| n-C₃H₇ |  | F | F |
| n-C₅H₁₁ | 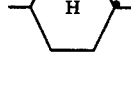 | H | H |
| n-C₅H₁₁ | 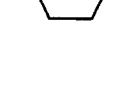 | H | F |

-continued

| R | —(A¹—Z¹)ₘ—A²—Z²— | L¹ | L² |
|---|---|---|---|
| n-C₅H₁₁ | (cyclohexyl-H)—(phenyl with F at 3,5 positions) | F | F |

Example 18 a) 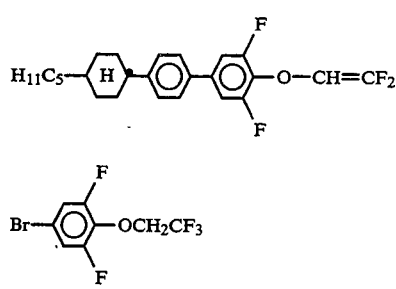

0.085 mol of 4-bromo-2,6-difluorophenol is dissolved in 100 ml of 1,3-dimethyl-2-imidazolidinone (DMEU), the solution is heated to 140° C., and 0.09 ml of 2,2,2-trifluoroethylmethyl sulfonate is added dropwise. The solution is stirred at 140° C. for 24 hours. 500 ml of ice water are subsequently added, and the mixture is subjected to customary work-up.

b) 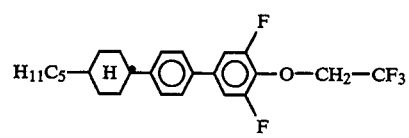

0.05 mol of trans-n-pentylcyclohexylphenylboric acid, 20 ml of toluene, 10 ml of ethanol, 0.030 mol of sodium carbonate and 0.86 mmol of tetrakis(triphenylphosphine)palladium(0) are added to 0.015 mol of 4-bromo-2,6-difluorophenol 2,2,2-trifluoroethyl ether, and the mixture is refluxed for 2 hours. 100 ml of petroleum ether (40°–80°) are added, and the mixture is subjected to customary work-up.

c) 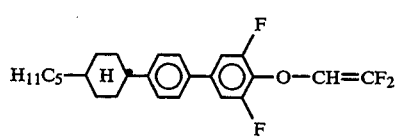

13.5 mmol of diisopropylamine are added dropwise at —20° C. to 13.5 mmol of BuLi (15% in n-hexane) in 10 ml of THF. The solution is subsequently stirred for 10 minutes and added dropwise at —40° C. under a protective gas to a mixture comprising 10 ml of THF, 13.5 mmol of trans-n-pentylcyclohexylphenyl-2,6-difluorophenol 2,2,2-trifluoroethyl ether. The mixture is stirred first at —40° C. for 0.5 hour and subsequently at room temperature overnight. After hydrolysis, the mixture is subjected to customary work-up. C 31 N 103 I The following compounds of the formula

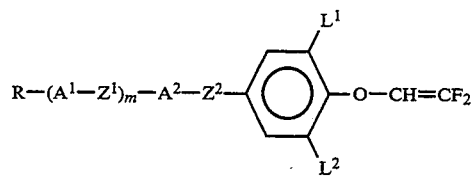

are prepared analogously.

| R | —(A¹—Z¹)ₘ—A²—Z²— | L¹ | L² |
|---|---|---|---|
| n-C₃H₇ | phenyl | H | H |
| n-C₃H₇ | phenyl | H | F |
| n-C₃H₇ | phenyl | F | F |
| n-C₅H₁₁ | phenyl | H | H |
| n-C₅H₁₁ | phenyl | H | F |
| n-C₅H₁₁ | phenyl | F | F |
| CH₃CH₂O | phenyl | H | F |
| CH₂=CHCH₂CH₂ | phenyl | F | F |
| C₂H₅ | cyclohexyl-cyclohexyl | F | F |
| n-C₃H₇ | cyclohexyl-cyclohexyl | H | F |
| CH₂=CHCH₂CH₂ | cyclohexyl-cyclohexyl | H | H |

-continued
| R | $-(A^1-Z^1)_m-A^2-Z^2-$ | $L^1$ | $L^2$ |
|---|---|---|---|
| n-C₃H₇ | 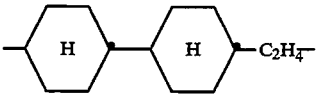 | H | H |
| n-C₅H₁₁ | 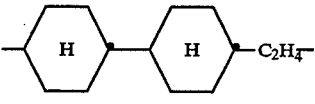 | H | F |
| CH₃CH₂OCH₂ | 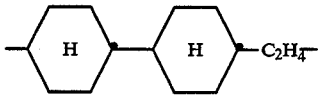 | F | F |
| n-C₃H₇ | 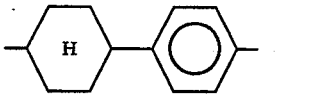 | H | F |
| n-C₃H₇ | 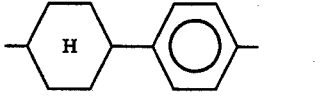 | F | F |
| n-C₅H₁₁ | 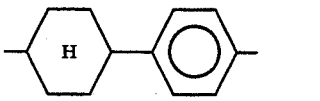 | H | H |
| n-C₅H₁₁ | 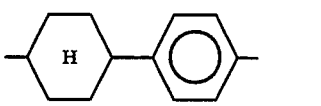 | F | H |
| n-C₃H₇ | 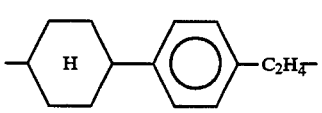 | H | H |
| n-C₅H₁₁ | 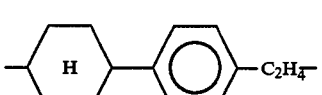 | H | F |
| n-C₅H₁₁ | 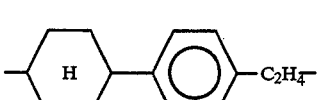 | F | F |
| n-C₃H₇ | 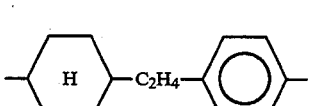 | H | H |
| n-C₃H₇ |  | H | F |
| n-C₅H₁₁ |  | F | F |
-continued
| R | $-(A^1-Z^1)_m-A^2-Z^2-$ | $L^1$ | $L^2$ |
|---|---|---|---|
| n-C₅H₁₁ | 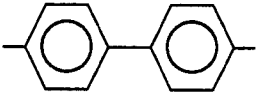 | H | H |
| n-C₅H₁₁O | 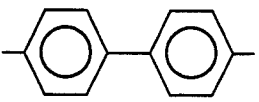 | H | F |
| CH₃OCH₂ | 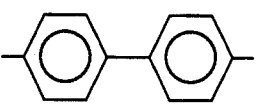 | F | F |
| n-C₃H₇ | 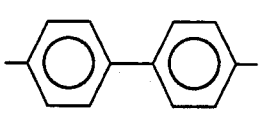 | H | H |
| n-C₄H₉ | 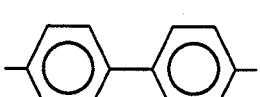 | H | F |
| n-C₅H₁₁ | 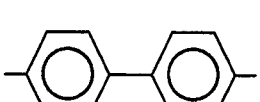 | F | F |
| n-C₃H₇ | 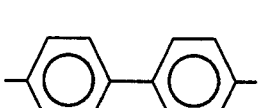 | H | F |
| n-C₅H₁₁ |  | H | F |
| n-C₅H₁₁ |  | F | F |
| n-C₃H₇ | 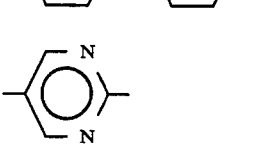 | H | H |
| n-C₂H₅ |  | H | H |
| n-C₂H₅ |  | H | F |
| n-C₄H₉ |  | F | F |

-continued

| R | $-(A^1-Z^1)_m-A^2-Z^2-$ | $L^1$ | $L^2$ |
|---|---|---|---|
| n-C$_4$H$_9$ | ⬡H—⬡H— | H | H |
| n-C$_3$H$_7$ | ⬡H—⬡H— | H | H |
| n-C$_3$H$_7$ | ⬡H—⬡H— | F | F |
| n-C$_5$H$_{11}$ | ⬡H—⬡H— | H | H |
| n-C$_5$H$_{11}$ | ⬡H—⬡H— | H | F |

We claim:

1. Vinyl compounds of the formula I

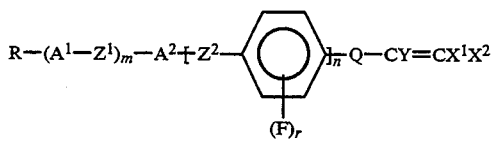

in which
R is H, an alkyl or alkenyl radical having 1 to 15 carbon atoms which is unsubstituted or monosubstituted by halogen, CN or CF$_3$, or an alkyl or alkenyl radical as described above wherein one or more CH$_2$ groups in the radical is replaced, independently of one another, by —O—, —CO—, —CO—O—, or —O—CO— such that oxygen atoms are not linked directly to one another, A$^1$ and A$^2$ are each, independently of one another, a
 (a) trans-1,4-cyclohexylene radical in which, optionally, one or more non-adjacent CH$_2$ groups are replaced by —O— and/or —S—, or a 1,4-cyclohexenylene radical, or
 (b) 1,4-phenylene radical in which, optionally, one or two CH groups are replaced by N,
where the radicals (a) and (b) are optionally substituted by CN or fluorine, Z$^1$ and Z$^2$ are each, independently of one another, —CO—O—, —O—CO—, —CH$_2$O—, —OCH$_2$—, —CH$_2$CH$_2$—, —CH═CH—, —C≡C— or a single bond, and one of the radicals Z$^1$ and Z$^2$ is alternatively —(CH$_2$)$_4$— or —CH═CH—CH$_2$CH$_2$—,
Q is —O—,
X$^1$ is H, F or Cl,
X$^2$ is F, Cl, CF$_3$ or SF$_5$,
Y is H, F or Cl,
r is 0 to 4,
n is 0 or 1, and
m is 0, 1, 2 or 3 where m+n≧1.

2. Compounds of claim 1 of the formula I8

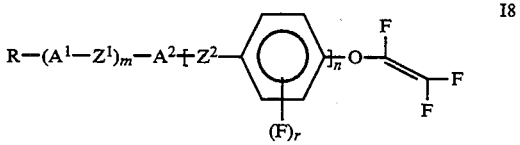

in which R, A$^1$, Z$^1$, A$^2$, Z$^2$, m, n and r are as defined in claim 1.

3. Compounds of claim 1 of the formula I10

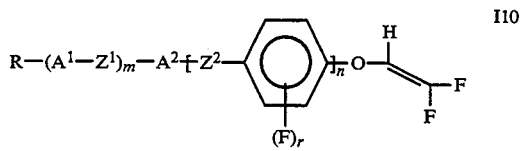

in which R, A$^1$, Z$^1$, A$^2$, Z$^2$, m, n and r are as defined in claim 1.

4. Compounds of the formula I10 of claim 3 in which r is 0.

5. A liquid-crystalline medium comprising at least two liquid-crystalline components, wherein at least one component is a compound of the formula I of claim 1.

6. A liquid-crystalline display element, comprising a liquid-crystalline medium according to claim 5.

7. An electro-optical display element, comprising, as dielectric, a liquid-crystalline medium according to claim 5.

8. A liquid-crystalline medium comprising one or more compounds of the formula I of claim 1.

9. Vinyl compounds of claim 1 of the formula II 1

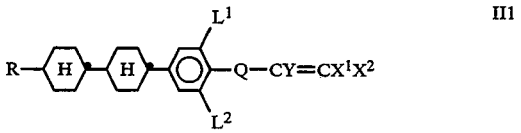

in which R, Q, Y, X$^1$ and X$^2$ are as defined in claim 1, and L$^1$ and L$^2$ are independently H or F.

10. Vinyl compounds of claim 1 of the formula II 3

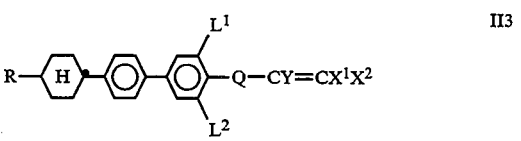

in which R, Q, Y, X$^1$ and X$^2$ are as defined in claim 1, and L$^1$ and L$^2$ are independently H or F.

11. Vinyl compounds of claim 1 of the formula II 6

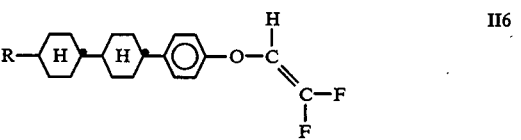

wherein R has the meaning given in claim 1.

12. Vinyl compounds of claim 1 of the formula II 12
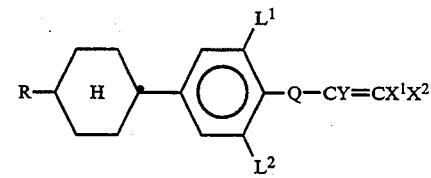
13. Vinyl compounds of claim 1 of the formula
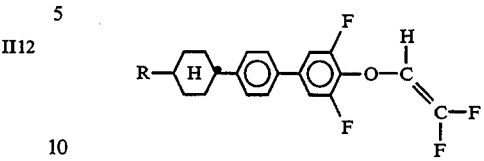
in which R, Q, Y, $X^1$ and $X^2$ are as defined in claim 1, and $L^1$ and $L^2$ are independently H or F.
wherein R has the meaning given in claim 1.
* * * * *

UNITED STATES PATENT AND TRADEMARK OFFICE
CERTIFICATE OF CORRECTION

PATENT NO. : 5,403,512
DATED : April 4, 1995
INVENTOR(S) : Ekkehard BARTMANN et al.

It is certified that error appears in the above-indentified patent and that said Letters Patent is hereby corrected as shown below:

Title Page; Item [30] Under Foreign Application

Priority Data:

Insert:  June 05, 1991 [DE] Germany 41 18 425.4
        Dec. 05, 1991 [DE] Germany 41 40 135.2
        Mar. 17, 1992 [DE  Germany 42 08 551.9
          Apr. 03, 1992 [DE] Germany 42 11 150.1

Signed and Sealed this

Fifteenth Day of August, 1995

*Attest:*

BRUCE LEHMAN

*Attesting Officer*     *Commissioner of Patents and Trademarks*